US007935131B2

(12) United States Patent
Anthamatten et al.

(10) Patent No.: US 7,935,131 B2
(45) Date of Patent: May 3, 2011

(54) SHAPE MEMORY POLYMERS

(75) Inventors: Mitchell L. Anthamatten, Rochester, NY (US); Jiahui Li, Rochester, NY (US)

(73) Assignee: University of Rochester, Rochester, NY (US)

( * ) Notice: Subject to any disclaimer, the term of this patent is extended or adjusted under 35 U.S.C. 154(b) by 897 days.

(21) Appl. No.: 11/820,693

(22) Filed: Jun. 20, 2007

(65) Prior Publication Data

US 2008/0177303 A1    Jul. 24, 2008

Related U.S. Application Data

(60) Provisional application No. 60/854,249, filed on Oct. 25, 2006.

(51) Int. Cl.
*A61B 17/04*    (2006.01)
*C08F 26/06*    (2006.01)

(52) U.S. Cl. ....... 606/231; 606/151; 623/1.15; 128/864; 526/302; 526/312; 526/263; 526/264

(58) Field of Classification Search .................. 606/231, 606/151; 623/1.15; 128/864; 526/302, 312, 526/263, 264
See application file for complete search history.

(56) References Cited

U.S. PATENT DOCUMENTS

| 6,538,089 B1 | 3/2003 | Samra et al. |
| 2005/0017396 A1 | 1/2005 | Pearce et al. |

OTHER PUBLICATIONS

Cate et al., "Enantioselective Cyclization of Racemic Supramolecular Polymers," *Journal of American Chemical Society*, 125:6860-6861 (2003).

Geurts et al., "Syntheses of New Amino-Functionalized Methacrylates and Their Use in Free Radical Polymerizations," *Journal of Applied Polymer Science*, 80:1401-1415 (2001).
Lendlein et al., "Shape Memory Polymers," *Angew. Chem. Int. Ed.*, 41:2034-2057 (2002).
Yamauchi et al.,"Thermoreversible Poly(alkyl acrylates) Consisting of Self-Complementary Multiple Hydrogen Bonding," *Macromolecules*, 36:1083-1088 (2003).
Ahir et al.; Self-Assembled Shape-Memory Fibers of Triblock Liquid-Crystal Polymers; Advanced Functional Materials, 2000; pp. 1-6.
Brunsveld et al.; Supramolecular Polymers; Chemical Reviews, 2001, vol. 101; pp. 4071-4097.
Cao et al.; Hydrogen-bonded polymer network-poly(ethylene glycol) complexes with shape memory effect; Journal Mater. Chem., 2002, vol. 12; pp. 2957-2960.
Cates; Nonlinear Viscoelasticity of Wormlike Micelles (and Other Reversibly Breakable Polymers); Journal of Phys. Chem., 1990, vol. 94; pp. 371-375.
Cates; Reptation of Living Polymers: Dynamics of Entangled Polymers in the Presence of Reversible Chain-Scission Reactions; Macromolecules, 1987, vol. 20; pp. 2289-2296.
Chino et al.; Themoreversible Cross-Linking Rubber Using Supramolecular Hydrogen-Bonding Networks; Macromolecules, 2001, vol. 34; pp. 9201-9204.
Diab et al.; Polymer Complexes: Part VIII—Thermal Stability of Poly(2-Acrylamidopyridine) and Polymer Complexes of 2-Acrylamidopyridine with Some Transition Metal Chlorides; Polymer Degradation and Stability, 1989, vol. 24; pp. 51-58.
Farnik et al.; Synthesis and Self Assembly of Hydrogen-Bonded Supramolecular Polymers; Macromol. Symp., 2004, vol. 217; pp. 247-266.

(Continued)

*Primary Examiner* — Robert D. Harlan
(74) *Attorney, Agent, or Firm* — Hodgson Russ LLP

(57) ABSTRACT

The present disclosure relates to Shape Memory Polymers (SMP's) comprising function groups that allow the polymers to be elastically deformed, utilized in the elastically deformed state, and subsequently returned to the original polymorphic shape.

47 Claims, 6 Drawing Sheets

OTHER PUBLICATIONS

Hirschberg et al.; Supramolecular Polymers from Linear Telechelic Siloxanes with Quadruple-Hydrogen-Bonded Units; Macromolecules, 1999, vol. 32; pp. 2696-2705.

Irie; Chapter 9: Shape memory polymers; Otsuka and Wayman eds.; Shape Memory Materials, 1998; Cambridge University Press; pp. 203-219.

Jeong et al.; Shape memory polyurethane containing amorphous reversible phase; Journal of Materials Science, 2000, vol. 35; pp. 1579-1583.

Jiang et al.; Light-Induced Shape Change in Elastomers and Gels; Polymers Move in Response to Light; Advanced Materials, 2006, vol. 18, No. 11; pp. 1471-1475.

Kim et al.; Polyurethanes having shape memory effects; Polymer, 1996, vol. 37; No. 26; pp. 5781-5793.

Lendlein et al.; Biodegradable, Elastic Shape-Memory Polymers for Potential Biomedical Applications; Science, 2002, vol. 296; pp. 1673-1676.

Lendlein et al.; Shape-Memory Polymer Networks from Oligo (ε-caprolactone)Dimethacrylates; Journal of Polymer Science: Part A: Polymer Chemistry, 2005, vol. 43; pp. 1369-1381.

Lendlein et al.; Light-induced shape-memory polymers; Nature, 2005, vol. 434; pp. 879-882.

Lin et al.; Study on Shape-Memory Behavior of Polyether-Based Polyurethanes. I. Influence of the Hard-Segment Content; Journal of Applied Polymer Science, 1998, vol. 69; pp. 1563-1574.

Liu et al.; Shape Memory of Hydrogen-Bonded Polymer Network/Poly(ethylene glycol) Complexes; Macromolecules, 2004, vol. 37; pp. 228-2232.

Liu et al.; Chemically Cross-Linked Polycyclooctene: Synthesis, Characterization, and Shape Memory Behavior; Macromolecules, 2002, vol. 35; pp. 9868-9874.

Rabani et al.; Synthesis and characterization of two shape-memory polymers containing short aramid hard segments and poly(ε-caprolactone) soft segments; Polymer, 2006, vol. 47; pp. 4251-4260.

Sakurai et al.; Crystal transformation of styrene-butadiene block copolymer; Polymer, Sep. 1994, vol. 35; pp. 4238-4239.

Sherrington et al.; Self-assembly in synthetic macromolecular systems via multiple hydrogen bonding interactions; Chem. Soc. Rev., 2001, vol. 30; pp. 83-93.

Sijbesma et al.; Reversible Polymers Formed from Self-Complementary Monomers Using Quadruple Hydrogen Bonding; Science, 1997, vol. 278; pp. 1601-1604.

Sivakova et al.; Utilization of a Combination of Weak Hydrogen-Bonding Interactions and Phase Segregation to Yield Highly Thermosensitive Supramolecular Polymers; J. Am. Chem. Soc., 2005, vol. 127; pp. 18202-18211.

Sontjens et al.; Stability and Lifetime of Quadruply Hydrogen Bonded 2-Ureido-4[1H]-pyrimidinone Dimers; J. Am. Chem. Soc., 2000, vol. 122; pp. 7487-7493.

Suzuki et al.; Supramolecular Crosslinked Linear Poly(Trimethylene Iminium Trifluorosulfonimide) Advanced Materials, 2006, vol. 18; pp. 1043-1046.

Tobushi et al.; Thermomechanical properties in a thin film of shape memory polymer of polyurethane series; Smart Mater. Struct., 1996, vol. 5; pp. 483-491.

Toensmeier; Compounders Thwart Counterfeiting With Covert Additive Techniques; Plastics Engineering, 2005; pp. 10-11.

Wubbenhorst et al.; Complex Dynamics of Hydrogen Bonded Self-assembling Polymers; IEEE Transactions on Dielectrics and Electrical Insulation, Jun. 2001, vol. 8, No. 3; pp. 365-372.

Xu et al.; Synthesis and shape memory effects of Si-O-Si cross-linked hybrid polyurethanes; Polymer, 2006, vol. 47; pp. 457-465.

Zheng et al.; Shape memory properties of poly(D,L-lactide)/hydroxyapatite composites; Biomaterials, 2006, vol. 27; pp. 4288-4295.

Diab et al.; Polymer Complexes: Part VI—Thermal Stability of Poly(2-Acrylamidophenol) Homopolymer and Complexes of Poly(2-Acrylamidophenol) with Some Transition Metal Salts; Polymer Degradation and Stability, 1988, vol. 23; pp. 83-90.

STRAIN

% UPy = polymers formed from reactions wherein 1 and 2 mole % of Hydrogen Bonding monomers having the $R^4$ unit with the formula:

were employed as starting materials.

SHAPE MEMORY POLYMERS

CROSS REFERENCE TO RELATED APPLICATIONS

This application claims priority to the U.S. Provisional Application No. 60/854,249, filed Oct. 25, 2006, the disclosure of which application is hereby incorporated in its entirety by this reference.

FIELD OF THE DISCLOSURE

The present disclosure relates to Shape Memory Polymers (SMP's) that have surprising properties wherein the polymers can be elastically deformed, utilized in the elastically deformed state, and subsequently returned to the original polymorphic shape.

BACKGROUND OF THE DISCLOSURE

Most materials behave elastically at low levels of strain. For crystalline solids and amorphous glasses, elasticity occurs up to a strain limit rarely exceeding 1%. Elastic strain is related to the extent to that atoms are dislodged from their equilibrium positions. However, elasticity in polymers is very different, and polymeric materials can exhibit elastic behavior to several hundred percent strain. Polymeric elastomers are usually high molecular weight molecules, well above their glass transition temperature $T_G$, and they typically contain a network of chemical or physical crosslinks that act as permanent entanglements and restrict long range (irreversible) slippage of chains. When a polymer elastomer is stretched, a restoring force arises because molecular chains are distorted from their most probable and preferable configuration—this phenomenon is known as entropic elasticity. Several classes of polymers exhibit entropic elasticity, including natural and synthetic rubbers and polyurethanes.

Entropy-based elasticity must be differentiated from the so called "shape-memory effect" defined by the literature. A shape-memory material is one that returns to its original shape only after the application of an external stimulus (Irie, "Shape Memory Materials." Chapter 9: "Shape Memory Polymers" Otsuka and Wayman eds. Campbridge University Press, 1998). For example, a thermo-responsive shape-memory material returns to its "remembered" shape only upon heating past a critical shape-memory temperature $T_{SM}$. Above $T_{SM}$ such a material can be elastically deformed by subjecting it to external stresses, and then cooling it (while under stress) beneath $T_{SM}$. In the cooled state, external stresses can be removed and the material retains its deformed shape. Upon subsequent heating above $T_{SM}$, the material recovers its elastic strain energy and returns to its original shape. Metallic alloys and ceramics are well-known to exhibit this shape-memory effect. Shape-memory polymers (SMP's) are noted for their ability to recover extremely large strains—up to several hundred percent—that are imposed by mechanical loading. The large-strain recovery observed in SMP's is a manifestation of entropy elasticity.

SMP's offer tremendous advantages to the fields of biotechnology and medicine (Lindlein et al., "Shape Memory Polymers" Angew. Chem. Int. Ed. 41, p 2034 (2002)). By exploiting the large-strain recovery of SMP's, surgeons can implant bulky objects into the body through small incisions. Biodegradable SMP's enable the development of degradable sutures and vascular stents. Biological MicroElectroMechanic Systems (Bio-MEMS) can perform intricate gripping, releasing, or even stitching operations. SMP's can also be used in non-biological applications including rewritable storage media, intelligent packaging materials, shapeable tools, and deployable objects for space exploration. SMP's can also be used in the development of recyclable thermosets and materials processing.

Solid state elastomers that utilize thermoreversible self-association of functional groups offer a novel way to stabilize mechanically deformed states, and the potential of such materials as shape-memory materials has not previously been studied. Therefore, there is a long felt need in the art for shape memory polymers containing self-associating chemical crosslinkers.

SUMMARY OF THE DISCLOSURE

The present disclosure meets the aforementioned needs in that it has been surprisingly discovered that incorporation of certain functional groups into polymer backbones affords these polymers the ability to conserve, or mechanically stabilize elastically deformed states of strain in polymeric materials.

The present disclosure relates to shape memory polymers having the formula:

$$-[HB]_x-[MOD]_y-[XL]_z-$$

comprising:
i) hydrogen bonding units, HB, having at least one hydrogen bond donor moiety and at least one hydrogen bond acceptor moiety;
ii) backbone modifier units, MOD; and
iii) crosslinking units, XL, that are capable of forming one or more irreversible crosslinks;
the index x is from about 0.5 to about 20, the index y is from about 75 to about 99.6, and the index z is from about 0.1 to about 5;
wherein the polymer is characterized by having a shape memory temperature, $T_{SM}$, such that the polymer can be elastically deformed at the shape memory temperature, and subsequently lowered to a shape memory freezing temperature, $T_F$, and the method of elastic deformation is removed, the polymer will return to its, original shape with a rate slower than the rate observed if the method of mechanical elastic deformation were removed at $T_{SM}$; provided the shape memory freezing temperature $T_F$ is above the glass transition, $T_G$, of the polymer, and provided the polymer is in the amorphous state at $T_F$.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE DISCLOSURE

Figure 1:
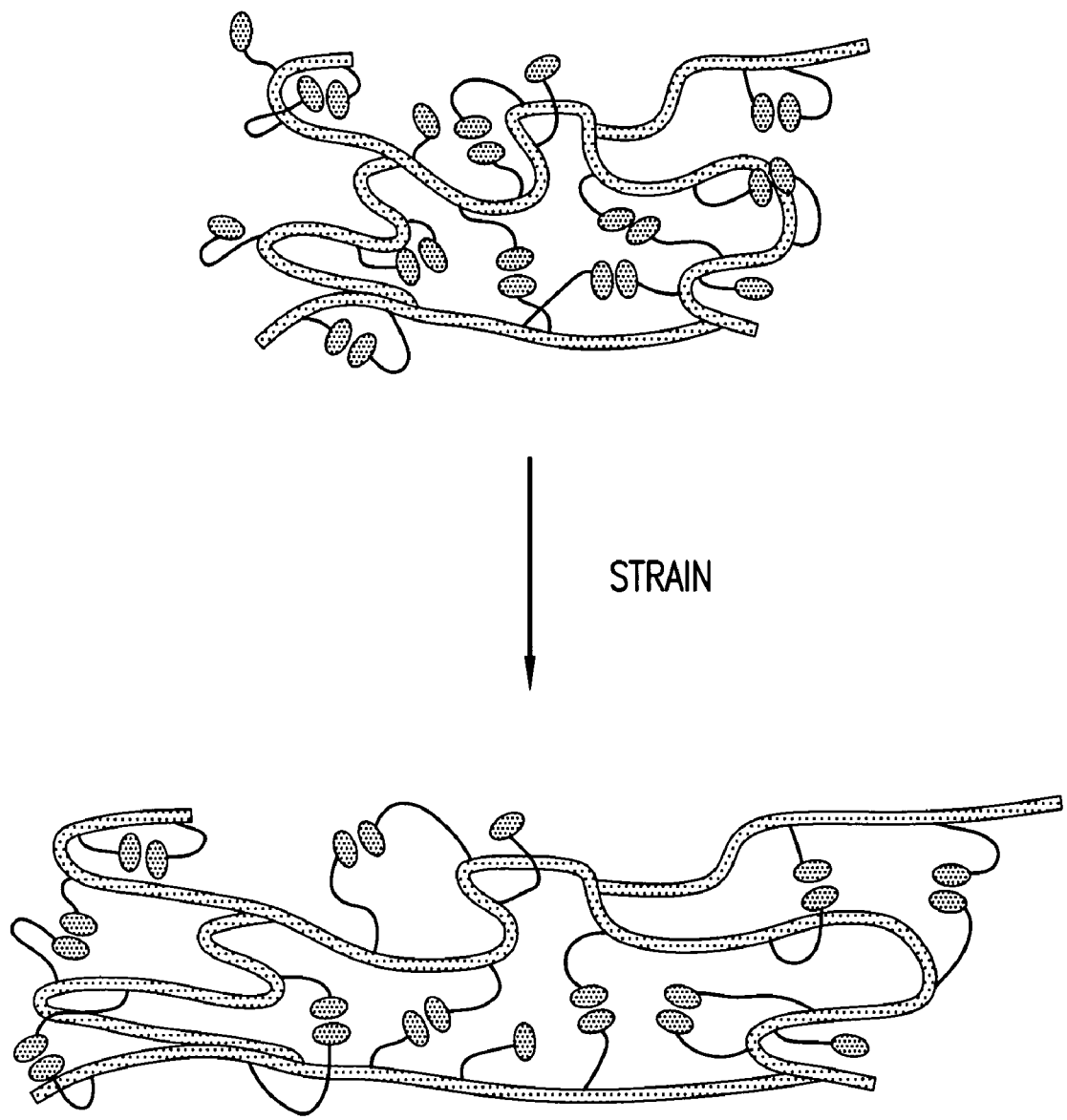
FIG. 1. is a schematic of how the Shape Memory Polymers disclosed herein re-associate after being elastically strained.

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A weight percent of a component, unless specifically stated to the contrary, is based on the total weight of the formulation or composition in which the component is included.

By "sufficient amount" and "sufficient time" means an amount and time needed to achieve the desired result or results, e.g., dissolve a portion of the polymer.

"Admixture" or "blend" is generally used herein means a physical combination of two or more different components. In the case of polymers, an admixture, or blend, of polymers is a physical blend or combination of two or more different polymers as opposed to a copolymer that is single polymeric material that is comprised of two or more different monomers.

"Molecular weight" as used herein, unless otherwise specified, refers generally to the relative average chain length of the bulk polymer. In practice, molecular weight can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the Inherent Viscosity determined from a dilute polymer solution using a particular set of concentration, temperature, and solvent conditions.

The term "number average molecular weight" ($M_n$) is defined herein as the mass of all polymer molecules divided by the number of molecules that are present.

The term "weight average molecular weight" ($M_w$) is defined herein as the mass of a sample of a shape memory polymer divided by the total number of molecules that are present.

The present disclosure relates to Shape Memory Polymers (SMP's) having surprising properties. The Shape Memory Polymers of the present disclosure have three distinct features and/or advantages:
  i) the SMP's are transparent to light at all processing temperatures; they have no glassy or crystalline domains that can scatter light;
  ii) the SMP's exhibit amorphous or rubbery "fixed" states; thereby providing a malleable polymer that functionality can be taken advantage of for permanent as well as temporary uses; and
  iii) the SMP's can be precisely tuned to have differential recovery rates and recovery temperatures based upon the specific need of the formulator.

The Shape memory Polymers of the present disclosure consist of a crosslinked polymer containing reversibly associating side-groups. A schematic of the polymer architecture is shown in FIG. 1. When the material is elastically strained, self-complementary side-groups associate to temporarily hold or "pin" the material in its strained state. Since the association of side-groups is a completely reversible process, the material slowly relaxes to its original, equilibrium shape. From an architectural standpoint, the material can be viewed as having covalent crosslinks that are superimposed onto dynamic, non-covalent crosslinks. The material stiffness is determined by the number of covalent crosslinks, and its shape recovery rate is determined by the number of non-covalent crosslinks and the dynamics of associating side-groups.

The polymers of the present disclosure have a unique combination of properties due to their constituent units that allow the polymers to be deformed or elastically strained from a first shape or size, then subsequently become temporarily pinned into a second deformed or elastically strained state. The hydrogen bonds formed by the Hydrogen Bonding Units described herein below, serve to lock or pin the polymers into the second state. The polymers of the present disclosure can be returned to the initial state by one of three ways described herein below.

Typically the shape memory polymers are elastically deformed or strained at a particular temperature, the shape memory temperature, $T_{SM}$, that is particular for each application for which the polymer is used and is unique to each polymeric species. First the polymer is raised to a temperature, $T_{SM}$, that provides necessary energy for fast dissociation of existing hydrogen bonds between various units and thereby enables the deformation of the polymer into the desired second shape or configuration. Then the polymer is elastically strained by an applied mechanical force and subsequently cooled to a temperature that is referred to herein as the shape memory freezing temperature, $T_F$, that is also unique to each species of polymer and can be manipulated by the formulator, usually by selection of the type and number of hydrogen bonding units in the polymer. After cooling to the shape memory freezing temperature, the mechanical load is removed. During cooling and before the mechanical elastically straining force is removed, the hydrogen bonding units begin to form new local hydrogen bonds with other units also capable of forming hydrogen bonds. These newly formed hydrogen bonds now serve to lock or pin the polymer into the deformed or strained configuration.

A single hydrogen bond is relatively weak, typically on the order of 5 to 40 kJ/mol. By increasing or decreasing the number of hydrogen bonding units, and, therefore, the number of possible hydrogen bonds capable of being formed within a molecule, the formulator can adjust both the shape memory temperature, as well as the shape memory freezing temperature. However, since one of the advantages of the present polymers is their light transparency and amorphous state, the shape freezing temperature, $T_F$, can be well above the glass transition temperature, $T_G$.

The polymers of the present disclosure also exhibit characteristic strain recovery and mechanical creep that are properties of the particular species and can be adjusted by the formulator. If, for example a mechanical load is applied, cumulative hydrogen bond forces stabilize the polymer's mechanical state, resisting creep. The mechanical creep rate depends on temperature and is much faster at higher temperatures. Furthermore, if a mechanical load is removed, cumulative hydrogen bonds stabilize the polymer's strained state, resisting shape recovery. Likewise, the rate of shape recovery depends on temperature and is much faster at higher temperature. However, the shape memory polymers disclosed herein can be elastically strained by any method that distends the polymer, for example thermally, electrically, and the like.

Figure 2:
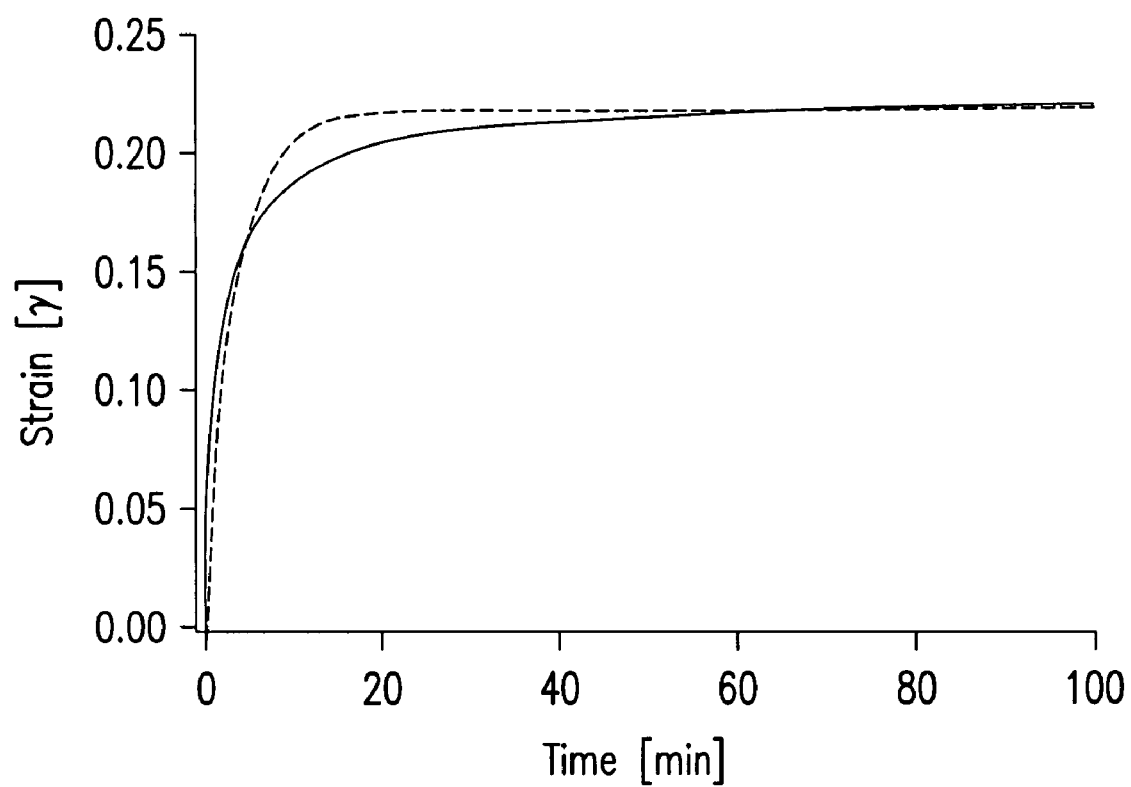
FIG. 2. is a graph of the isothermal (47° C.) creep data for the polymer of Example 4 using a 50 mN tensile load (solid line) and the least-squares fit of these data to the non-linear constitutive model (dotted line).
Figure 3:
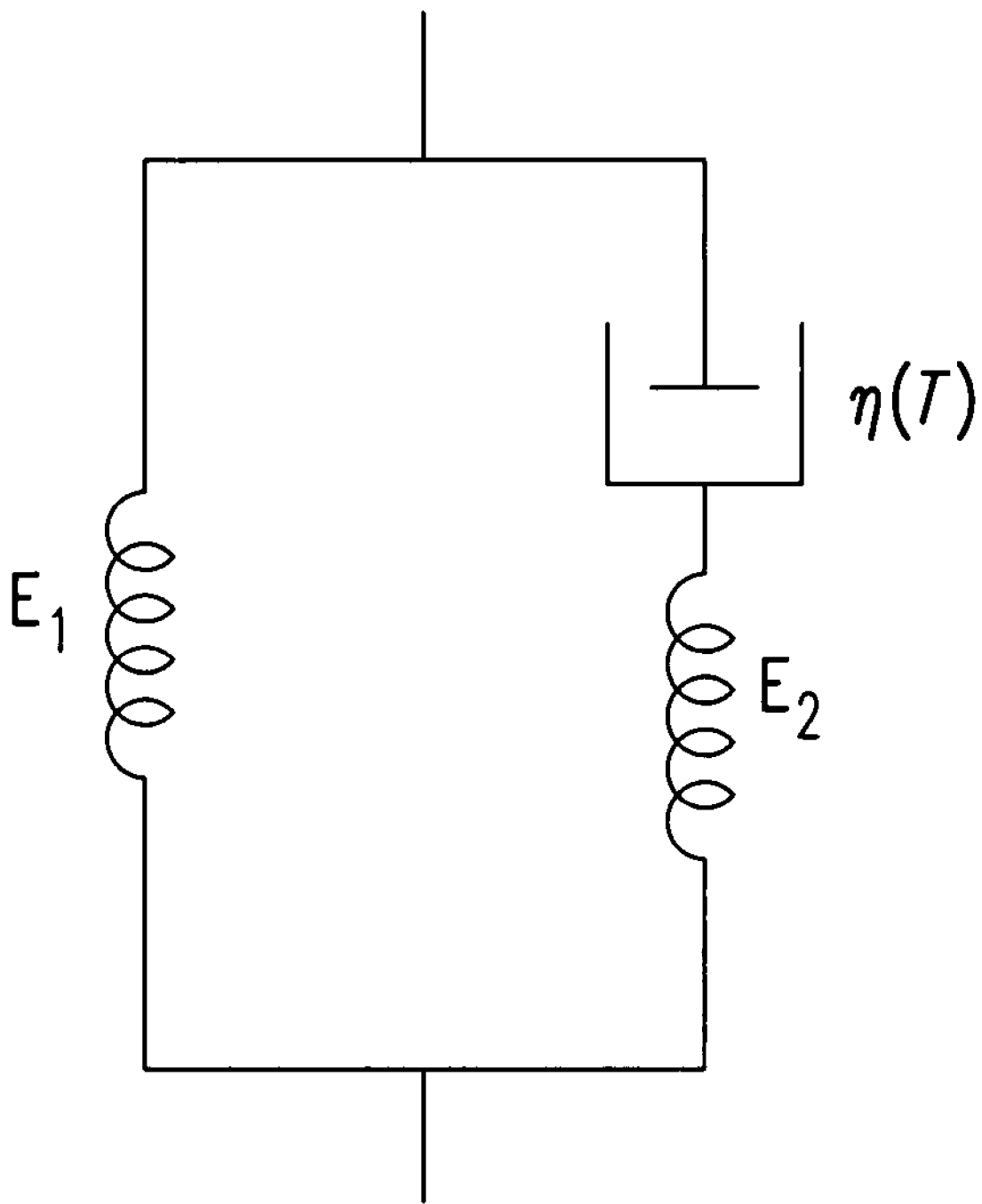
FIG. 3. is a diagram showing the mechanical elements of the constitutive model: spring element ($E_1$) and Maxwell element ($E_2$, $\eta(T)$) in series.

Mechanical creep behavior and shape recovery can be studied using a thermogravimetric analysis apparatus. FIG. 2 represents the isothermal mechanical creep data acquired on the polymer described in Example 4 herein below. The measurement temperature was 47° C. and the mechanical load was 50 mN. The dotted line represents the line derived from the mathematical model derived from the constitutive equation below, whereas the solid line represents a least-square fit to the data using a simple model such as that shown in FIG. 3. In FIG. 1, $E_1$ and $E_2$ refer to the elastic moduli corresponding to the springs in the model and $\eta(T)$ refers to the temperature dependent viscosity that is typically measured isothermally in order to design into the polymer the desired recovery rate at the temperature at which the polymer will be used. $E_1$ describes the polymer's instantaneous response to a stress and $E_2$ and $\eta(T)$ taken in series with one another represent a Maxwell element. The constitutive equation for this model is:

$$(E_1 + E_2)\sigma + \eta(T)\frac{d\sigma}{dt} = E_1 E_2 \gamma + E_1 \eta(T) \frac{d\gamma}{dt} \qquad \text{Equation 1}$$

where $\sigma$ is applied stress and $\gamma$ is polymer elongation. For a creep experiment, the initial condition is $\gamma=0$ and the boundary condition is specified by the applied load, i.e. $\sigma$ is constant.

Figure 4:
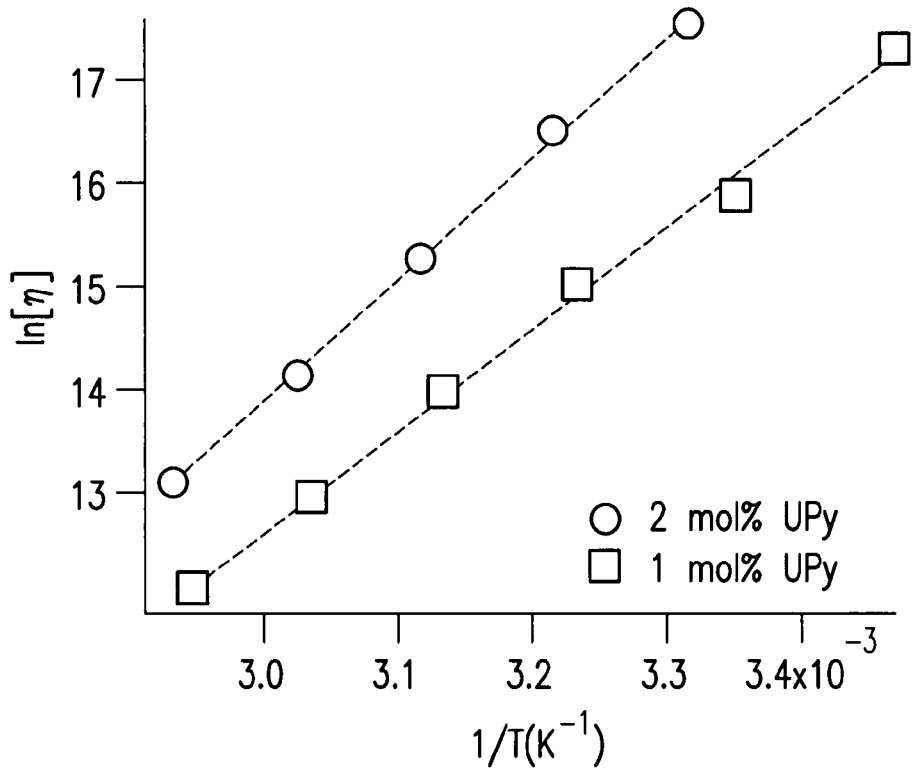
FIG. 4. depicts the Arrhenius temperature-dependence of fitted viscosities obtained from creep data for the polymers of Examples 4 and 5 measured at various temperatures.
Figure 4:
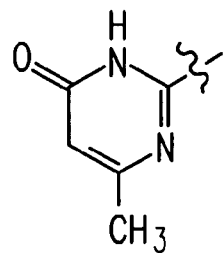

Non-linear least square regression fits to Equation 1 using isothermal creep data, such as those shown in FIG. 2, result in values for $E_1$, $E_2$, and $\eta$. A plot of $\ln(\eta)$ against inverse temperature is shown in FIG. 4 for two of the samples discussed herein. By utilizing data such as those found in FIG. 4, the formulator can determine the relative rate of elongation change, $d\gamma/dt$, and therefore the relaxation rate or creep for a particular polymer.

Figure 5:
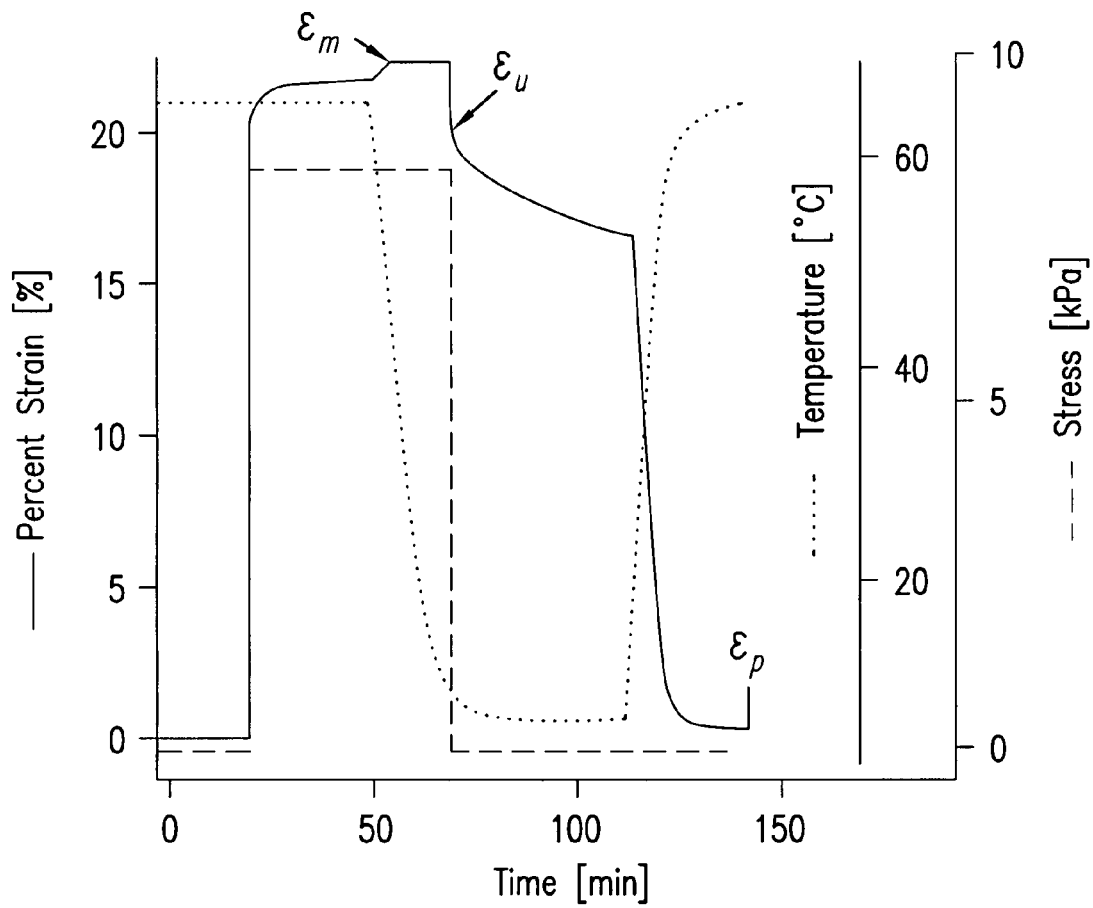
FIG. 5. depicts the shape-memory response curve of the polymer of Example 4.

FIG. 5 depicts an example of the shape-memory response curve for the polymer of Example 4. Shape-memory response curves such as this can be utilized by the formulator to determine the effects that adjustments in the polymer composition will have on relaxation times and other features of the polymer's shape memory response. For example, the solid line in FIG. 4 indicates the percent strain of the polymer at a particular temperature. As the data indicate, the polymer of Example 4 was first equilibrated at the $T_{SM}$ (66° C.) for 20 minutes after which a mechanical force of 50 mN was applied. This force resulted in rapid elongation (solid line) of the shape memory polymer. While maintaining the 50 mN applied force, the temperature of the shape memory polymer was then lowered to the $T_F$ (5° C.). Cooling the polymer furthers its elongation to its maximum ($\epsilon_m$, solid line) that is due to entropy elasticity, and will vary in amount from species to species. Once the polymer is equilibrated at the $T_F$ temperature, the mechanical force is removed and the polymer begins to creep back to its original state at a relaxation rate depicted by the section of the curve immediately following $\epsilon_u$. This rate of deformation is slow but can be accelerated by increasing temperature. As can be seen in FIG. 4, there is a sharp inflection in the curve at the point wherein the temperature of the polymer is raised above the $T_F$. The formulator, by extrapolating outward the curve of percent strain (level of relaxation) versus time measured isothermally at $T_F$, will be able to determine how long it will take the shape-memory polymer to return to the original state. This information will allow the formulator to determine the effects on polymer relaxation rates that adjustments in the relative amounts of polymer constituents will have.

The polymers of the present disclosure are comprised of three types of units:
  i) Hydrogen Bonding Units—HB;
  ii) Backbone Modifying Units—MOD; and
  iii) Crosslinking Units—XL.

Each of these units fulfills a function that affects the properties of the final polymer. The Hydrogen Bonding Units serve to form temporary crosslinks between polymer chains (inter chain hydrogen bonding) or semi-permanent crosslinks between other hydrogen bonding units of the same polymer chain (intra chain hydrogen bonding). These HB units serve to temporarily "pin" the polymers of the present disclosure into an elastically strained state. While HB units do undergo dissociation below $T_F$, at low temperatures (below $T_F$) the dissociation rate is slow enough that the polymer remains elongated for relevant application timescales.

The formulator, by incorporating more or less hydrogen bonding units into the shape memory polymer will be able to control the relaxation rate or creep recovery of the polymer back as it returns to its original form (permanent shape) at a given temperature. For a given temperature, increasing the number of hydrogen bonding units will cause a slower relaxation rate, while decreasing the number of hydrogen bonding units will cause the polymer to have a faster relaxation rate. In addition, the number of crosslinking units and their length will also affect the relaxation rate.

One way in which the formulator can cause the polymers to rapidly relax into the original state is to raise the temperature of the material above the shape memory temperature, $T_{SM}$, or to a temperature above it. Raising the temperature of the polymer above $T_F$ will also increase the rate of creep, but at a slower rate than raising the temperature to $T_{SM}$ or above.

The present disclosure utilizes the term "hydrogen bond" in the same manner as the artisan of ordinary skill. The terms "hydrogen bond acceptor moiety" and "hydrogen bond donor moiety" are defined herein as "moieties that are capable when at least one acceptor moiety is present and at least one donor moiety is present, of forming a hydrogen bond."

The following are non-limiting examples of the hydrogen bonding formed by the units that comprise the shape memory polymers of the present disclosure:

i) an example of two similar units that are capable of forming two hydrogen bonds between the units.

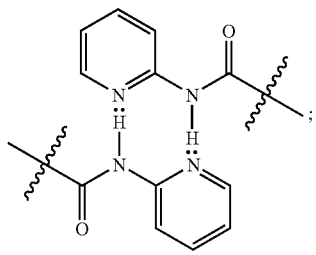

ii) an example of two different units that are capable of forming three hydrogen bonds between the units.

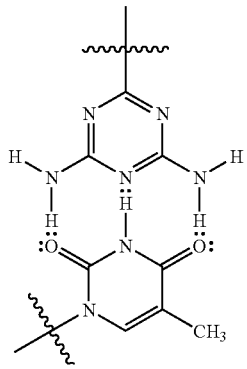

iii) an example of a hydrogen bonding unit wherein hydrogen bonds are formed between Z units (donors) and $R^4$ units (acceptors) that are further described herein below. Those of ordinary skill in the art will also recognize the presence of a potential intra moiety hydrogen bond (arrow) that can help further determine the orientation of the Z and $R^4$ units relative to one another by further assisting in holding the hydrogen bonding units in alignment.

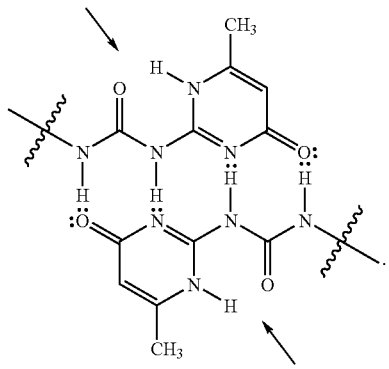

It will be understood by the artisan of ordinary skill, that other refinements and changes to the Q units defined herein below via modification of $R^4$, W, Y, and Z, that are also further defined herein below, will provide variation in the degree of hydrogen bonding. As shown below, substitution of the ring N—H units will be another means for the formulator to adjust the alignment of hydrogen bonding units in the Q units of the present disclosure, for example, the units having the formula:

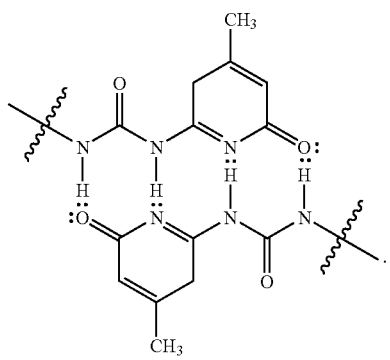

As will be seen further herein below in the description of the present disclosure, the formulator will have great latitude in choosing units that will provide more or less hydrogen bonding, and therefore provide the formulator with a method for varying the properties of the shape memory polymers. The propitious choice of $R^4$ units, mixtures, or variations in $R^4$ will allow the formulator profound latitude in creating various arrays of hydrogen bonds.

The following chemical hierarchy is used throughout the specification to describe and enable the scope of the present disclosure and to particularly point out and distinctly claim the units that comprise the compounds of the present disclosure, however, unless otherwise specifically defined, the terms used herein are the same as those of the artisan of ordinary skill. The term "hydrocarbyl" stands for any carbon atom-based unit (organic molecule), the units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" and are used to divide hydrocarbyl units into cyclic and non-cyclic classes.

As it relates to the following definitions, "cyclic hydrocarbyl" units may comprise only carbon atoms in the ring (carbocyclic and aryl rings) or may comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:
   For the purposes of the present disclosure the term "substituted and unsubstituted acyclic hydrocarbyl" encompasses 3 categories of units:
   1) linear or branched alkyl, non-limiting examples of that include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
   2) linear or branched alkenyl, non-limiting examples of which include, ethenyl ($C_2$), 3-propenyl ($C_3$), 1-propenyl (also 2-methylethenyl) ($C_3$), isopropenyl (also 2-methyl-ethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
   3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_9$), 5-hydroxy-5-ethylhept-3-ynyl ($C_9$), and the like.

B. Substituted and Unsubstituted Cyclic Hydrocarbyl:
   For the purposes of the present disclosure the term "substituted and unsubstituted cyclic hydrocarbyl" encompasses 5 categories of units:
   1) The term "carbocyclic" is defined herein as "encompassing rings comprising from 3 to 20 carbon atoms, wherein the atoms that comprise the rings are limited to carbon atoms, and further each ring can be independently substituted with one or more moieties capable of replacing one or more hydrogen atoms." The following are non-limiting examples of "substituted and unsubstituted carbocyclic rings" that encompass the following categories of units:
      i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
      ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).
      iii) carbocyclic rings that are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.
   2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" that encompass the following categories of units:
      i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
      ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).
   3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring that comprises the heteroatom is also not an aromatic ring." The following are non-limiting examples of "substituted and unsubstituted heterocyclic rings" that encompass the following categories of units:
      i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_9$), and 1,2,3,4-tetrahydro-quinoline ($C_9$).
      ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).
   4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings that comprises a heteroatom is an aromatic ring." The following are non-limiting examples of "substituted and unsubstituted heterocyclic rings" that encompass the following categories of units:
      i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)
ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_9$), quinoxalinyl ($C_9$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) that are connected to another moiety, unit, or core of the molecule by way of a $C_1$-$C_6$ alkylene unit. Non-limiting examples of tethered cyclic hydrocarbyl units include benzyl $C_1$-($C_6$) having the formula:

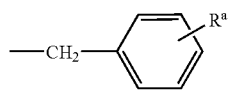

wherein $R^a$ is optionally one or more independently chosen substitutions for hydrogen. Further examples include other aryl units, inter alia, (2-hydroxyphenyl)Hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

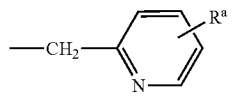

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, that comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

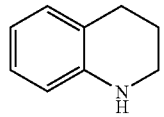

is, for the purposes of the present disclosure, considered a heterocyclic unit. 6,7-Dihydro-5H-cyclopentapyrimidine having the formula:

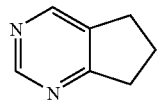

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

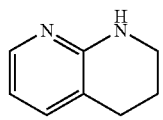

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, that has, one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form the substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units that can substitute for hydrogen atoms on a carbocyclic, aryl, heterocyclic, or heteroaryl unit:
i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
ii) —OR$^{30}$; for example, —OH, —OCH$_3$, —OCH$_2$CH$_3$, —OCH$_2$CH$_2$CH$_3$;
iii) —C(O)R$^{30}$; for example, —(OCH$_3$, —COCH$_2$CH$_3$, COCH$_2$CH$_2$CH$_3$;
iv) —C(O)OR$^{30}$; for example, —CO$_2$CH$_3$, —CO$_2$CH$_2$CH$_3$, —CO$_2$CH$_2$CH$_2$CH$_3$;

v) —C(O)N($R^{30}$)$_2$; for example, —CONH$_2$, —CONHCH$_3$, —CON(CH$_3$)$_2$;
vi) —N($R^{30}$)$_2$; for example, —NH$_2$, —NHCH$_3$, —N(CH$_3$)$_2$, —NH(CH$_2$CH$_3$);
vii) halogen: —F, —Cl, —Br, and —I;
viii) —CH$_m$X$_n$; wherein X is halogen, m is from 0 to 2, m+n=3; for example, —CH$_2$F, —CHF$_2$, —CF$_3$, —Cl$_3$, or —CBr$_3$; and
ix) —SO$_2$$R^{30}$; for example, —SO$_2$H; —SO$_2$CH$_3$; —SO$_2$C$_6$H$_5$ wherein each $R^{30}$ is independently hydrogen, substituted or unsubstituted C$_1$-C$_4$ linear, branched, or cyclic alkyl; or two $R^{30}$ units can be taken together to form a ring comprising 3-7 atoms. However, substituents that are suitable for replacement of a hydrogen atom are further defined herein below.

Shape Memory Polymers

The Shape Memory Polymers of the present disclosure are formed from the reaction of one or more monomers from each of the following three categories; hydrogen bonding monomers, backbone modifying monomers, and crosslinking monomers.

As it relates to the amount of hydrogen bonding units present in the polymers of the present disclosure, the following three primary categories are defined herein as:
i) lightly hydrogen bonded polymers: the initial reaction mixture prior to polymerization comprises from about 0.5 mole percent, mol %, to about 5 mol %, of a hydrogen bonding monomer;
ii) moderately hydrogen bonded polymers: the initial reaction mixture prior to polymerization comprises from about 5 mol % to about 10 mol %, of a hydrogen bonding monomer; and
iii) heavily hydrogen bonded polymers: the initial reaction mixture prior to polymerization comprises greater than about 10 mol %, of a hydrogen bonding monomer. A first aspect of heavily hydrogen bonded polymers relates to SMP's having from 10 mol % to 15 mol %, of a hydrogen bonding monomer. Another aspect of heavily hydrogen bonded polymers comprises from 15 mol % to 20 mol. %, of a hydrogen bonding monomer.

As it relates to the amount of crosslinking units present in the polymers of the present disclosure, the following four primary categories are defined herein as:
i) very lightly crosslinked polymers: the initial reaction mixture prior to polymerization comprises less than about 0.5 mole percent, mol %, of a crosslinking monomer;
ii) lightly crosslinked polymers: the initial reaction mixture prior to polymerization comprises from about 0.5 mole percent, mol %, to about 1.5 mol %, of a crosslinking monomer;
iii) moderately crosslinked polymers: the initial reaction mixture prior to polymerization comprises from about 1.5 mol % to about 2.5 mol %, of a crosslinking monomer; and
iv) heavily crosslinked polymers: the initial reaction mixture prior to polymerization comprises greater than about 2.5 mol %, of a crosslinking monomer. A first aspect of heavily crosslinked polymers relates to SMP's having from 2.5 mol % to 3.5 mol %, of a crosslinking monomer. Another aspect of heavily crosslinked polymers comprises from 3.0 mol % to 5 mol %, of a crosslinking monomer.

As is disclosed further herein below, crosslinking monomer also encompasses monomers having a moiety which after chain formation can serve to form crosslinks between polymer chains or within a polymer chain.

Mole percent, mol %, according to the present disclosure is calculated as in the example that follows. The three monomers:

i) a HB monomer having the formula:

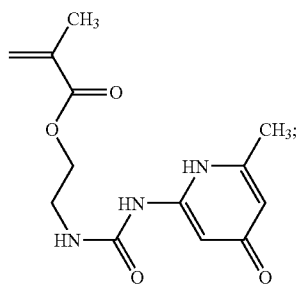

ii) a MOD monomer having the formula:

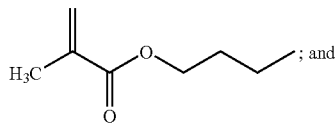

iii) a XL monomer having the formula:

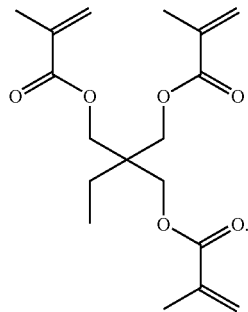

are admixed together prior to initiation of the polymerization reaction. The monomers have the following molecular weights respectively; HB=279.3 g/mol, MOD=142.2 g/mol, and XL=338.4 g/mol. The admixture comprises the following amount of each monomer:

| Monomer type | Mass (g) | Mol % |
| --- | --- | --- |
| MOD | 13.51 | 95 |
| HB | 0.56 | 2 |
| XL | 1.02 | 3 |

The resulting polymer from this admixture is a heavily crosslinked polymer as defined herein.

Hydrogen Bonding Units, HB

The shape-memory polymers of the present disclosure comprise hydrogen bonding units, HB, having the formula:

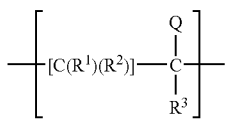

wherein each $R^1$ and $R^2$ is independently chosen from.
i) hydrogen;
ii) $C_1$-$C_6$ alkyl;
iii) halogen;
iv) cyano; and
v) phenyl;
$R^3$ is chosen from:
i) hydrogen; and
ii) $C_1$-$C_6$ alkyl.

The formulator may chose to use a single HB unit comprising monomer when forming the shape memory polymers of the present disclosure, or as described herein below, a mixture of hydrogen bonding monomers may be used. As it relates to the shape memory polymers of the present disclosure, one category of polymers comprises both $R^1$ and $R^2$ equal to hydrogen and $R^3$ equal to methyl. These HB units can be considered to be derivatives of methacrylic acid. A further category of polymers comprises $R^1$, $R^2$, and $R^3$ equal to hydrogen. These HB units can be considered to be derivatives of acrylic acid.

Q represents a unit having at least one hydrogen bond donor moiety and at least one hydrogen bond acceptor moiety. Q is further defined as a unit having the formula:

wherein L is a linking unit having the formula:

When the index i is equal to 1, the linking unit L is present, however, if the index i is equal to 0, the linking unit L is absent and $R^4$ is bonded directly to the polymer backbone providing a HB unit having the formula:

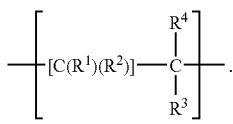

The expanded definition of Q, wherein the indices h, i, j, and k are each equal to 1, has the formula:

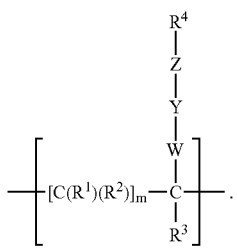

The hydrogen bonding backbone units are incorporated into the Shape Memory Polymers by way of HB monomers. An example of one category of HB monomers has the formula:

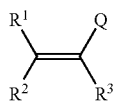

which when fully expanded has the formula:

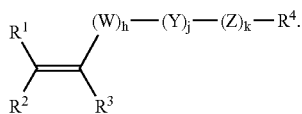

A first category of monomers relates to methacrylate-based monomers having the general formula:

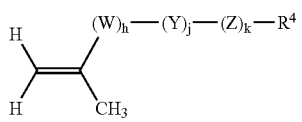

that are conveniently derived from methacrylic acid.

Another category of monomers relates to acrylate-based monomers having the general formula:

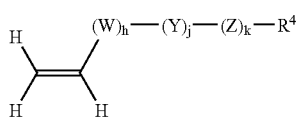

that are conveniently derived from acrylic acid.

As it relates to the position of the units that form the hydrogen bonds in the Q unit, it is not necessary that a hydrogen bonding acceptor or hydrogen bonding donor be present in any particular position, unit, or moiety; this is left to the prerogative of the formulator to increase and/or decrease the degree of potential hydrogen bond formation.

For example, in the first Category of HB units according to the present disclosure, hydrogen bonding donors and acceptors are found in the Z unit, as well as in the $R^4$ unit. For example, the Q unit having the formula:

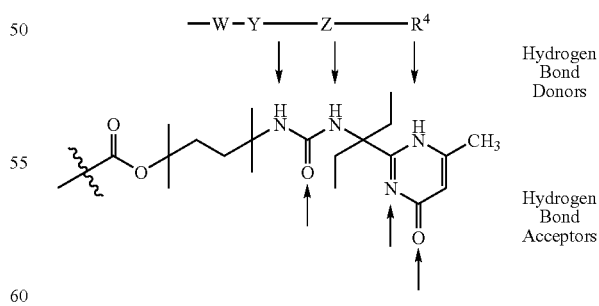

comprises hydrogen donors and acceptors in both the $R^4$ unit, as well as the Z unit. The categories of HB units will be set forth in detail herein below.

The units W and Z are each independently chosen from:
i) —C(O)—;
ii) —C(O)O—;

iii) —OC(O)—;
iv) —NH—;
v) —C(O)NH—;
vi) —NHC(O)—;
vii) NHC(O)NH—;
viii) —NHC(=NH)NH—; and
ix) —O—;

wherein the indices h and k are independently equal to 0 or 1. When the index h is 0 the W unit is absent, however, when h is equal to 1 the W unit is present. Likewise, when the index k is equal to 0 the Z unit is absent, however, when k is equal to 1 the Z unit is present.

Y is a unit having one dr more units chosen from:
i) —(CR$^{5a}$R$^{5b}$)$_s$—;
ii) —[(CR$^{5a}$R$^{5b}$)$_v$(CR$^{5a'}$R$^{5b'}$)$_u$]$_w$—;
ii) —[(CR$^{5a}$R$^{5b}$)$_t$O]$_w$—; or
iii) —[(CR$^{5a}$R$^{5b}$)$_t$O]$_w$(CR$^{5a}$R$^{5b}$)$_s$—;

wherein each R$^{5a}$ and R$^{5b}$ is independently chosen from:
i) hydrogen;
ii) hydroxyl; or
iii) C$_1$-C$_4$ alkyl;
R$^{5a'}$ and R$^{5b'}$ are each independently C$_1$-C$_4$ alkyl.

The index j is 0 or 1. When the index j is 0 the Y unit is absent, however, when j is equal to 1, the Y unit is present. The indices s, t, u, v, and w are each independent of one another and are defined as follows; the index s is from 0 to 10, the index t is from 2 to 10, the index u is from 1 to 10, the index v is from 1 to 10, the index w is from 1 to 10.

The first category of Y units relates to alkylene and alkyl substituted alkylene linking units having the formulae:

that provide for linking units comprising the same alkylene units or mixtures of different alkylene units.

The first aspect of the first category of Y units relates to Y units that comprise a (C$_2$) alkylene linking unit thereby providing Y units having the formula —CH$_2$CH$_2$— (ethylene). This unit is defined herein as Y equal to:

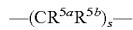

wherein all R$^{5a}$ and R$^{5b}$ units are hydrogen and the index s is equal to 2. Ethylene units can be used to connect any of the W and Z units described herein above. The following are non limiting examples of combinations of W and Z units that can be suitably combined with this first category of Y units (ethylene):

i)

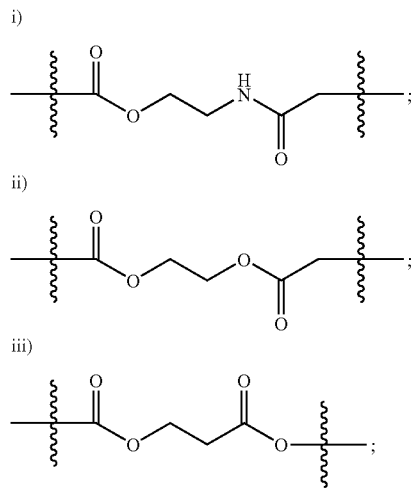

ii)

iii)

iv)

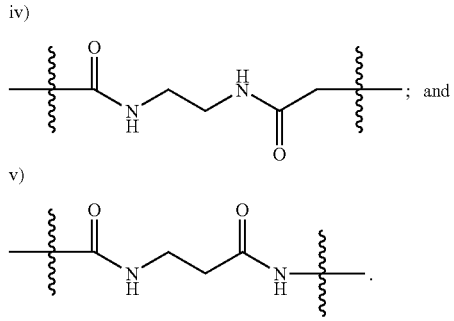

; and v)

The second aspect of the first category of Y units relates to C$_3$ alkylene linking units. There are two iterations of Y units encompassed within the second aspect of the first category of Y units. The first iteration relates to units wherein the index s is equal to 3 and each R$^{5a}$ and R$^{5b}$ is equal to hydrogen thereby providing a propylene unit having the formula: —CH$_2$CH$_2$CH$_2$—.

A non-limiting example of a Y unit comprising a propylene unit taken together with a W unit and Z unit has the formula:

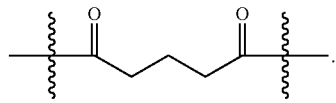

The second iteration of the second aspect of the first category of Y units relates to units having the formula:

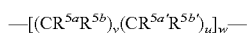

wherein the index v is equal to 1, the index u is equal to 1, and w can have the value from 1 to 10; R$^{5a}$ and R$^{5b}$ are each equal to hydrogen, R$^{5a'}$ is methyl and R$^{5b'}$ is hydrogen thereby providing the following two iso-propylene units having the formulae:

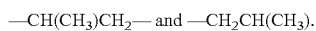

Non limiting examples of combinations of W and Z units that can be suitably combined with this second iteration of Y units include the following:

i) a Y unit wherein the index w is equal to 1 includes:

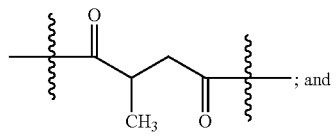

; and ii) a Y unit wherein the index w is equal to 2 includes:

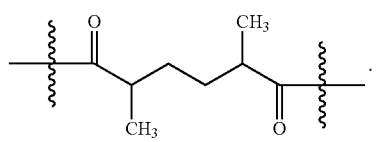

The third aspect of the first category of Y units relates to L linking units having the formula:

wherein each $R^{5a}$ and $R^{5b}$ is equal to hydrogen and the index s is from 4 to 10.

The first iteration of the third aspect of the first category of Y units relates to units wherein the index s is from 4 to 6, the units chosen from:
i) —CH$_2$CH$_2$CH$_2$CH$_2$—; (butylene)
ii) —CH$_2$CH$_2$CH$_2$CH$_2$CH$_2$—; (pentylene) and
iii) —CH$_2$CH$_2$CH$_2$CH$_2$CH$_2$CH$_2$—. (hexylene)

The second iteration of the third aspect of the first category of Y units relates to units wherein the index s is from 7 to 10, the units chosen from:
i) —CH$_2$CH$_2$CH$_2$CH$_2$CH$_2$CH$_2$CH$_2$—; (heptylene)
ii) —CH$_2$CH$_2$CH$_2$CH$_2$CH$_2$CH$_2$CH$_2$CH$_2$—; (octylene)
iii) —CH$_2$CH$_2$CH$_2$CH$_2$CH$_2$CH$_2$CH$_2$CH$_2$CH$_2$— (nonylene) and
iv) —CH$_2$CH$_2$CH$_2$CH$_2$CH$_2$CH$_2$CH$_2$CH$_2$CH$_2$CH$_2$—. (decylene)

The second category of Y units relates to alkyleneoxyalkylene units having the formula:

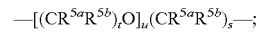

wherein the first aspect of the second category of Y units encompasses (C$_2$) ethyleneoxy units wherein the indices s and t are both equal to 2, each $R^{5a}$ and $R^{5b}$ unit is hydrogen, and u is from 1 to 10. Non-limiting examples of ethyleneoxy units in combination with a W and a Z unit include the following:

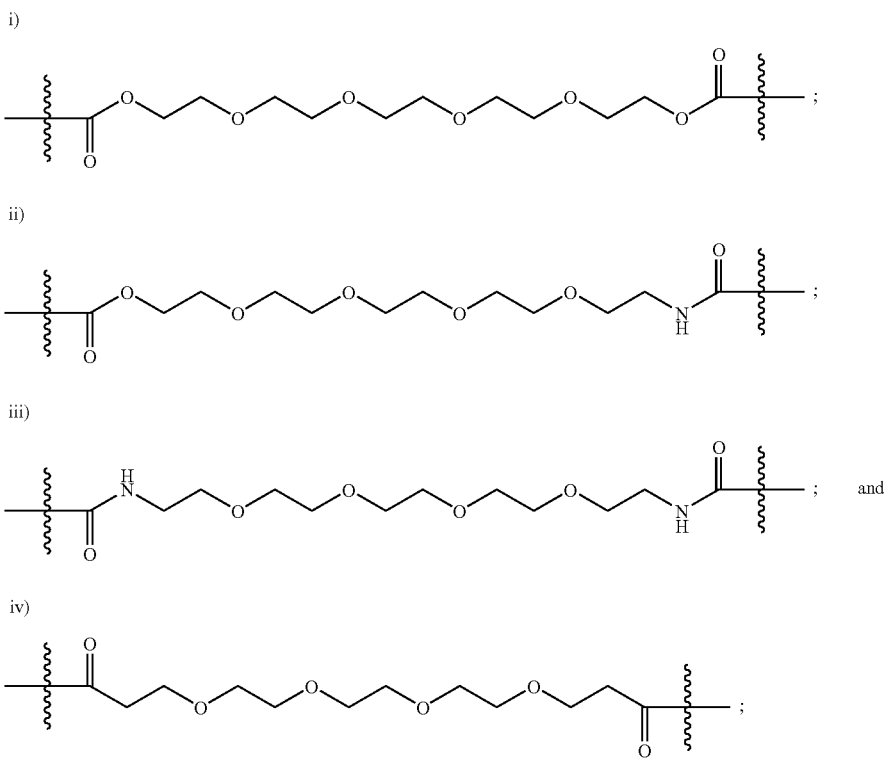

A second aspect of the second category of Y units relates to alkyleneoxyalkylene units having the formula:

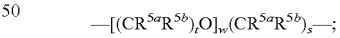

wherein at least one $R^{5a}$ unit of the Y unit is equal to methyl and the remaining non-methyl $R^{5a}$ units are hydrogen, while all the $R^{5b}$ units present are hydrogen. This aspect, therefore, encompasses at least one propyleneoxy (C$_3$) unit in the linking unit Y, non-limiting examples which when taken in combination with a W and a Z unit include the following:

i)
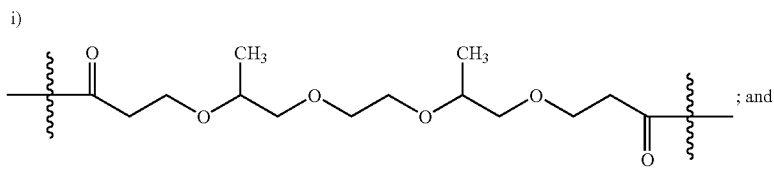

ii)

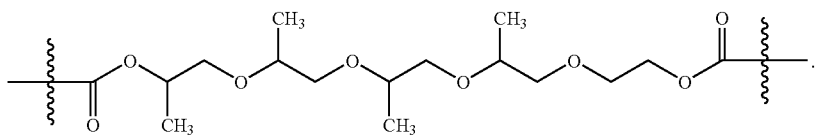

The third category of Y units relates to units wherein at least one $R^{5a}$ unit in the Y unit is equal to hydroxy, for example, a Y unit taken together with a W and a Z unit having the formula:

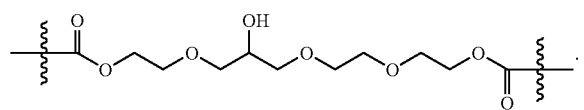

The artisan of ordinary skill will understand that units comprising a hydroxyl can be incorporated into Y units in various ways known in the art. As a non-limiting example, the two step process:

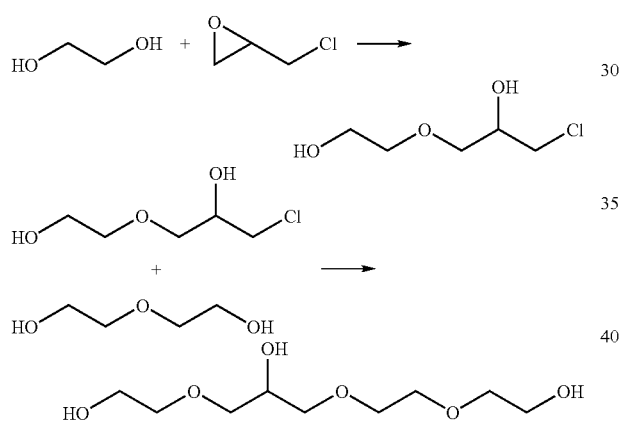

is one method that the artisan can use to prepare a unit containing a hydroxyl unit and that can then be linked to compatible W and Z units.

$R^4$ is a unit chosen from:
i) hydrogen;
ii) a substituted carbocyclic ring;
iii) a substituted aryl ring;
iv) a substituted or unsubstituted heterocyclic ring; or
v) a substituted of unsubstituted heteroaryl ring;

the substitution is a moiety capable of being a hydrogen bond donor or a hydrogen bond acceptor. Because carbocyclic and aryl rings do not comprise a hydrogen bond forming unit, they are substituted with one or more units that are capable of forming a hydrogen bond.

The first category of $R^4$ units relates to substituted or unsubstituted heterocyclic and heteroaryl rings.

The first aspect of the first category of $R^4$ units relates to substituted or unsubstituted $C_3$ or $C_4$ heterocyclic or heteroaryl 5-member rings, non-limiting examples of that are chosen from:

i) a pyrrolidinyl ring having the formula;

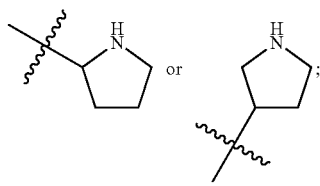

ii) a pyrrolyl ring having the formula:

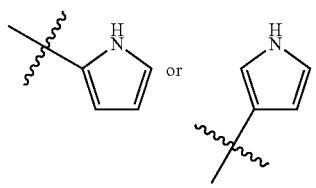

iii) a 4,5-dihydroimidazolyl ring having the formula:

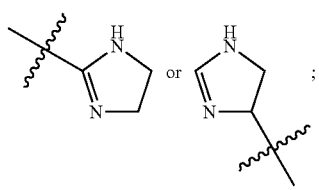

iv) an imidazolyl ring having the formula:

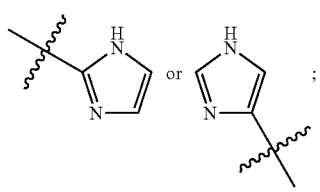

v) a pyrrolidinonyl ring having the formula:

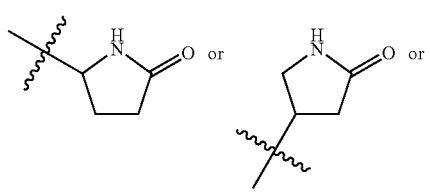

-continued

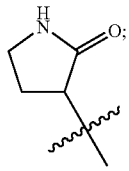

vi) an imidazolidinonyl ring having the formula:

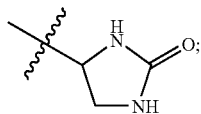

vii) an imidazol-2-only ring having the formula:

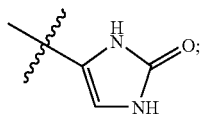

viii) an oxazolyl ring having the formula:

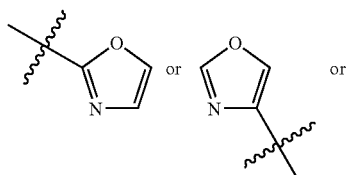

ix) a furanyl ring having the formula:

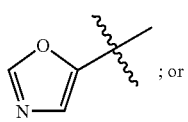

Rings belonging to this first category of $R^4$ can be substituted rings bonded to the balance of the HB unit via a nitrogen heteroatom, for example

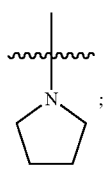

the units comprising one or more hydrogen bonding moieties, for example, pyrrolidinyl units derived from proline, hydroxyproline, or hydroxypyrrolidine having the formulae:

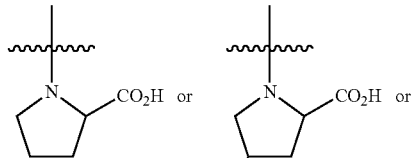

Other rings belonging to this category can be similarly substituted, for example,

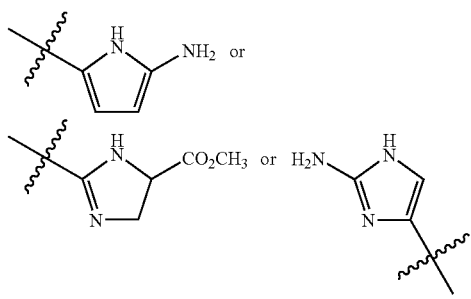

The second aspect of the first category of $R^4$ units relates to substituted or unsubstituted $C_3$, $C_4$ or $C_5$ heterocyclic or heteroaryl 6-member rings, non-limiting examples of which are chosen from:

i) a morpholinyl ring having the formula:

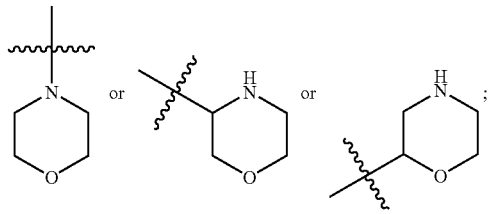

ii) a piperidinyl ring having the formula:

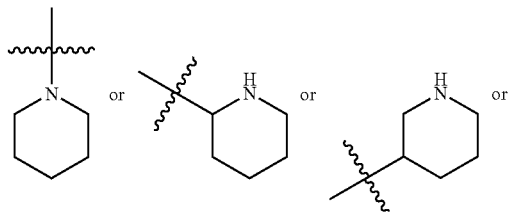

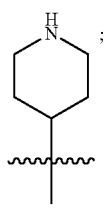
iii) a pyridinyl ring having the formula:
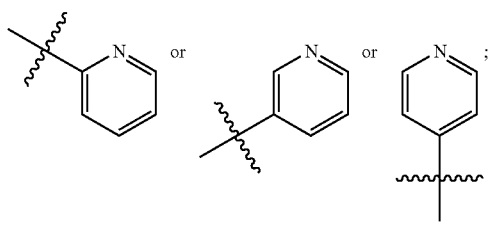
iv) a piperazinyl ring having the formula:
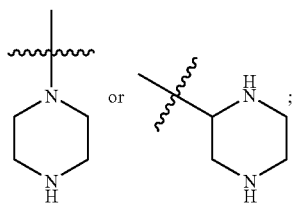
v) a ketopiperazinyl ring having the formula:
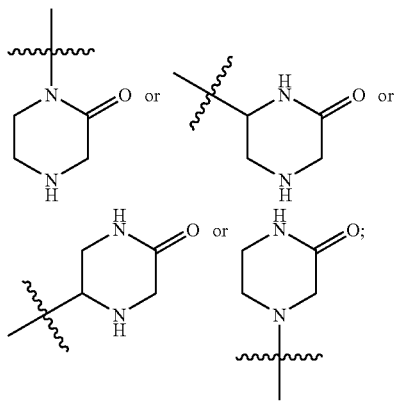
vii) a dihydropyrazin2-onyl ring having the formula:
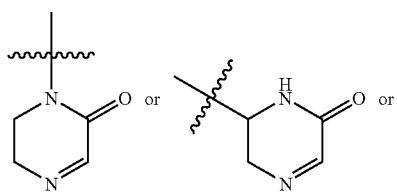
vii) a pyrazin-2-onyl ring having the formula:
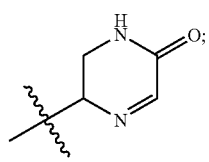
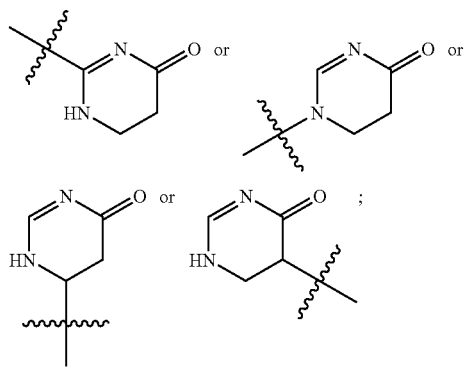
viii) dihydropyrimidin-4-onyl having the formula:
viii) a uracil ring having the formula:
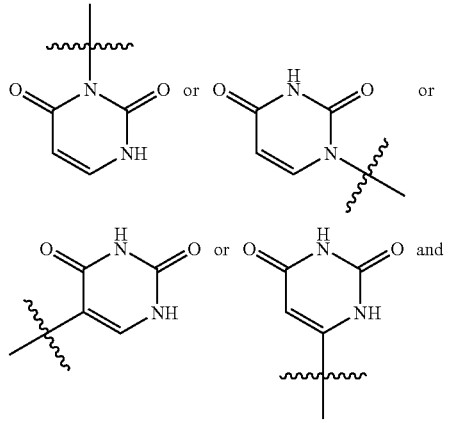

ix) a triazinyl ring having the formula:

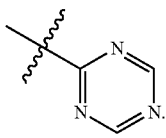

Hydrogen bonding units that are readily incorporated into the shape-memory polymers of the present disclosure include:

i) 6-methylpyrimidin-4-(1H)-on-2-yl having the formula:

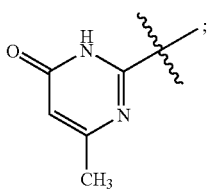

ii) 6-methylpyrimidin-4-(3H)-on-2-yl having the formula:

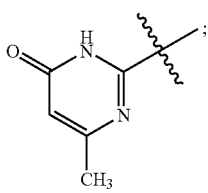

iii) 6-aminopyrimidin-4-(1H)-on-2-yl having the formula:

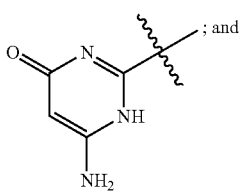

iv) 6-aminopyrimidin-4-(3H)-on-2-yl having the formula:

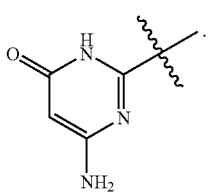

As is the case with the 5-member heterocyclic and heteroaryl rings, the 6-member rings can be substituted with one or more units capable of forming a hydrogen bond.

The third aspect of the first category of $R^4$ units relates to substituted or unsubstituted $C_4$, $C_5$, or $C_6$ heterocyclic or heteroaryl 9-member fused rings, non-limiting examples of which are chosen from:

i) purinyl rings having the formula:

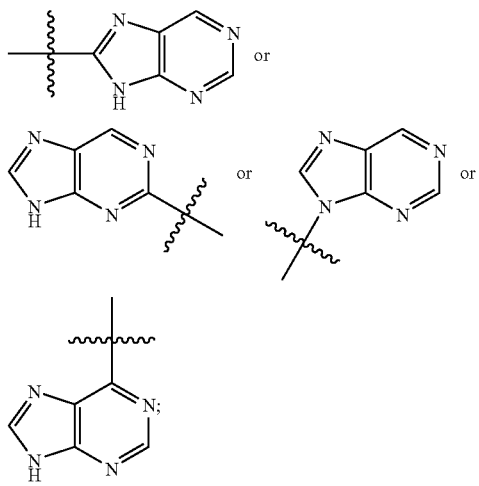

iii) amino purinyl rings having the formula:

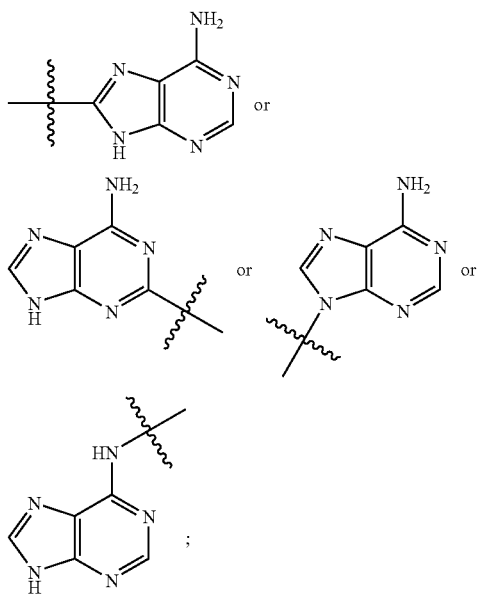

iii) aminopurinonyl rings having the formula:

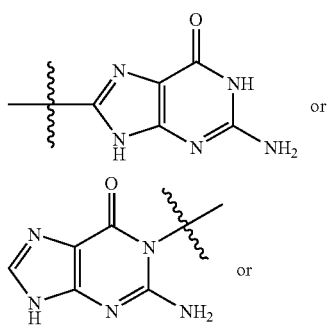

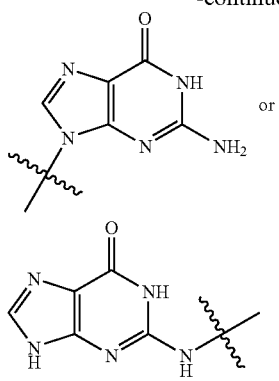

iv) pyrrolo[3,2-d]pyrimidinyl rings having the formula:

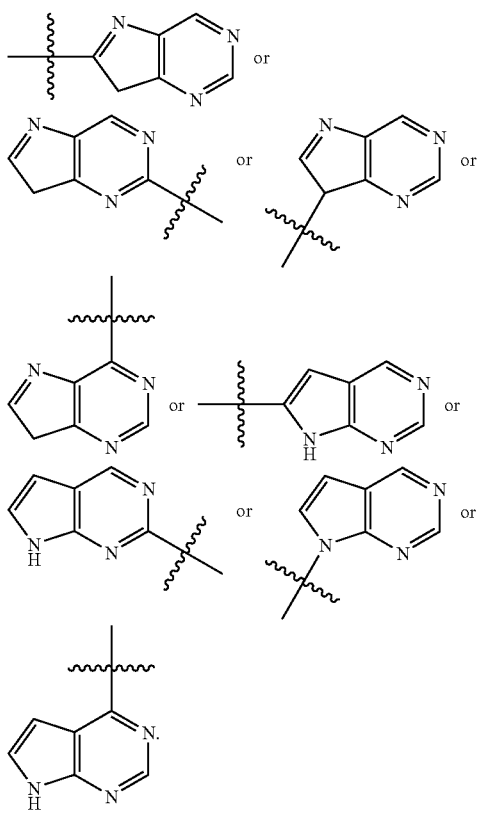

As is the case with the 5-member and 6-member heterocyclic and heteroaryl rings, the fused ring heterocyclic and heteroaryl units can be substituted with one or more units capable of forming a hydrogen bond.

As it relates to the substitutions that can replace a hydrogen atom on the heterocyclic or heteroaryl rings that comprise the $R^4$ units of the present disclosure, the following is a non-limiting description. Typically the substitutions are hydrogen bond accepting or hydrogen bond donating units, however, the alkyl units of the present disclosure are also acceptable substitutions for hydrogen. Without being limited by theory, the presence of alkyl substitutions may stabilize the ring or provide for a more favorable orientation. In addition to the substitutes for hydrogen defined herein above, the following are further non-limiting examples of substituents that are suitable for replacing a hydrogen atom of the $R^4$ units, the units are chosen from:

i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);

ii) —$NR^{6a}R^{6b}$; for example, —$NH_2$, —$NHCH_3$, —$N(CH_3)_2$, —$NHC_2H_5$, and —$N(C_2H_5)_2$;

iii) —$C(O)OR^7$; for example, —$C(O)OH$, —$C(O)OCH_3$; and —$C(O)OC_2H_5$;

iv) —$C(O)R^7$; for example, —$C(O)CH_3$; and —$C(O)C_2H_5$;

v) —$C(O)NR^{6a}R^{6b}$; for example, —$C(O)NH_2$, —$C(O)NHCH_3$, —$C(O)N(CH_3)_2$, —$C(O)NHC_2H_5$, and —$C(O)(C_2H_5)_2$;

vi) —$NR^8C(O)NR^{6a}R^{6b}$; for example, —$NHC(O)NH_2$, —$NHC(O)NHCH_3$, —$NHC(O)N(CH_3)_2$, —$NHC(O)NHC_2H_5$, and —$NHC(O)(C_2H_5)_2$;

vii) —$NR^8C(O)R^7$; for example, —$NHC(O)CH_3$, and —$NHC(O)C_2H_5$; and viii) —$NR^8C(=NR^8)NR^{6a}R^{6b}$; for example, —$NHC(=NH)NH_2$, —$NHC(=NH)NHCH_3$, —$NHC(=NH)N(CH_3)_2$, —$NHC(=NH)NHC_2H_5$, and —$NHC(=NH)(C_2H_5)_2$;

wherein $R^{6a}$, $R^{6b}$, $R^7$, and $R^8$ are each independently chosen from hydrogen, methyl, or ethyl.

The second category of $R^4$ units relates to substituted $C_6$ aryl (phenyl) and $C_{10}$ aryl (1-naphthyl and 2-naphthyl) units. The phenyl and naphthyl units that comprise the second category of $R^4$ units can be substituted with any of the units described herein above. Non-limiting examples of $C_6$ and $C_{10}$ substituted aryl units of the present disclosure include: 3-hydroxyphenyl, 4-hydroxyphenyl, 3,5-dihydroxyphenyl, 3-methoxyphenyl, 4-methoxyphenyl, 3,5-dimethoxyphenyl, 3-(dimethylamino)phenyl, 4-(dimethylamino)phenyl, 3-(acetyl)phenyl, 4-(acetyl)phenyl, 3-hydroxy-4-acetylphenyl, and the like.

The hydrogen bonding units of the present disclosure can be changed to fit the precise needs that are desired by the formulator. In addition to the selection of W and Z units, as well as $R^4$ units, the length of the linking unit L can be shortened or lengthened by changing or omitting W, Y, and Z units. This lengthening or shortening of the Y unit will provide the formulator with a method for controlling the tether to which the hydrogen bonding $R^4$ unit is attached and, therefore, the distance over which hydrogen bonds may be formed inter or intra molecularly. For example, beginning with acryloyl chloride a hydrogen bonding monomer comprising the following general formula:

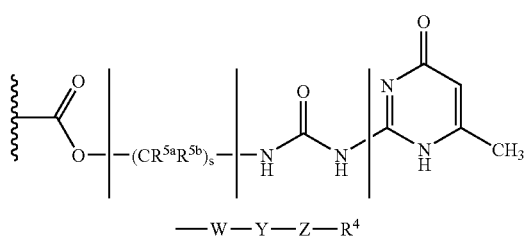

can be prepared over several steps, for example, by first reacting acryloyl chloride with a protected amino alcohol:

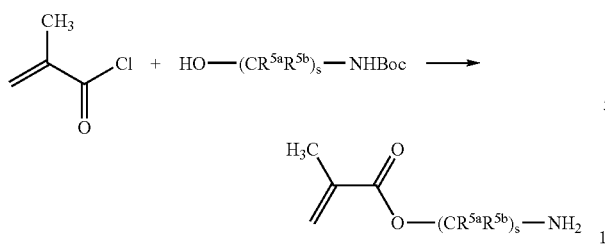

and thereby, a simple varying of the number of —(CR$^{5a}$R$^{5b}$)— units in the amino alcohol, will provide a method for modifying the length of the tether to fit the needs of the formulator. This intermediate can then be reacted with hydrogen bonding moieties to form hydrogen bonding, HB, monomers. For example, joining the intermediate formed above with a -Z-R$^4$ precursor unit:

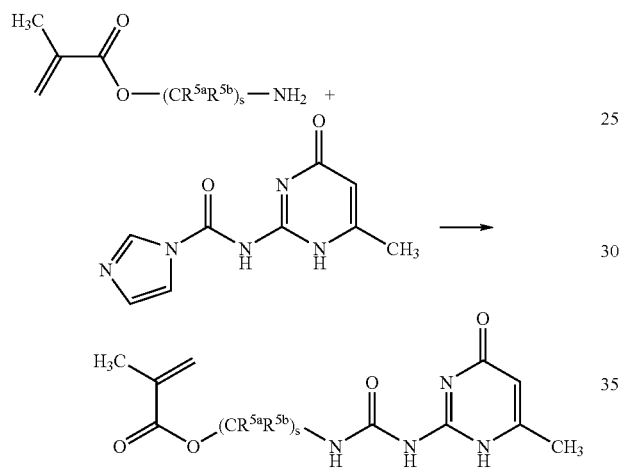

results in a hydrogen bonding monomer wherein the Y tether can be adjusted by the choice of initial reagents, as well as the R$^4$ and Z unit, to fit the variable needs of the formulator.

Another advantage of the present disclosure that the formulator can take into account when preparing the shape memory polymers of the present disclosure, is the differential rate at which hydrogen bonding units will "find" each other. For example, the more complex the hydrogen bonding unit, the long the time necessary for the units to locate a like hydrogen bonding unit once the elastically strained state is achieved. These more complex hydrogen bonding units will provide polymers having a slower relaxation time, but in addition, will also be provided a longer period of time when the polymer is initially elastically strained, wherein the formulator can make secondary adjustments to the shape memory polymer while the hydrogen bond ordering is occurring.

Backbone Modifier Units, Mod

The backbone modifier units of the present disclosure have the formula:

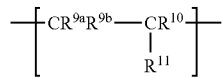

wherein each R$^{9a}$, R$^{9b}$, and R$^{10}$ is independently chosen from:
i) hydrogen; or
ii) C$_1$-C$_4$ alkyl; methyl (C$_1$), ethyl (C$_2$), n-propyl (C$_3$), iso-propyl (C$_3$), n-butyl (C$_4$), iso-butyl (C$_4$), sec-butyl (C$_4$), and tert-butyl (C$_4$).

R$^{11}$ is a unit chosen from;
i) hydrogen;
i) C$_1$-C$_4$ linear or branched alkyl; for example, methyl (C$_1$), ethyl (C$_2$), n-propyl (C$_3$), iso-propyl (C$_3$), n-butyl (C$_4$), iso-butyl (C$_4$), sec-butyl (C$_4$), and tert-butyl (C$_4$);
ii) —NR$^{12a}$R$^{12b}$; for example, —NH$_2$, —NHCH$_3$, —N(CH$_3$)$_2$, —NHC$_2$H$_5$, —N(C$_2$H$_5$)$_2$, —NHC$_3$H$_7$, —N(C$_3$H$_7$)$_2$, —N(CH$_3$)(C$_2$H$_5$), —N(CH$_3$)(C$_3$H$_7$), and —N(C$_2$H$_5$)(C$_3$H$_7$);
iii) —C(O)OR$^{13}$; for example,
a) —C(O)OH;
b) —C(O)OCH$_3$;
c) —C(O)OCH$_2$CH$_3$;
d) —C(O)OCH$_2$CH$_2$CH$_3$;
e) —C(O)OCH(CH$_3$)$_2$;
f) —C(O)OCH$_2$CH$_2$CH$_2$CH$_3$;
g) —C(O)OCH$_2$CH$_2$CH$_2$CH$_2$CH$_3$; and
h) —C(O)OCH$_2$CH$_2$CH$_2$CH$_2$CH$_2$CH$_3$;
iv) —C(O)R$^{13}$; for example,
a) —C(O)CH$_3$;
b) —C(O)CH$_2$CH$_3$;
c) —C(O)CH$_2$CH$_2$CH$_3$;
d) —C(O)CH(CH$_3$)$_2$;
e) —C(O)CH$_2$CH$_2$CH$_{12}$CH$_3$;
f) —C(O)CH$_2$CH$_2$CH$_2$CH$_2$CH$_3$; and
v) —C(O)NR$^{12a}$R$^{12b}$; for example, —C(O)NH$_2$, —C(O)NHCH$_3$, —C(O)N(CH$_3$)$_2$, —C(O)NHC$_2$H$_5$, and —C(O)NH(C$_2$H$_5$)$_2$;

wherein R$^{12a}$, R$^{12b}$, and R$^{13}$ are each independently hydrogen or C$_1$-C$_{10}$ alkyl.

As in the case of hydrogen bonding units, backbone modifier units are incorporated into the Shape Memory Polymer of the present disclosure by way of MOD monomers.

A first category of MOD monomers has the formula:

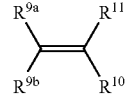

wherein R$^{9a}$ and R$^{9b}$ are each independently hydrogen or methyl (C$_1$), R$^{10}$ is chosen from hydrogen, methyl (C$_1$) and ethyl (C$_2$); R$^{11}$ is an ester or amide unit.

In a first aspect of the first category of backbone modifier units R$^{9a}$ and R$^{9b}$ are both hydrogen, R$^{10}$ is methyl (C$_1$), and R$^{11}$ is an ester unit having the formula C(O)OR$^{13}$; providing a monomer having the formula:

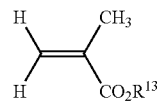

wherein R is chosen from methyl (C$_1$), ethyl (C$_2$), n-propyl (C$_3$), n-butyl (C$_4$), n-pentyl (C$_5$), n-hexyl (C$_6$), and n-heptyl (C$_7$); thereby providing a backbone modifier unit having the formula:

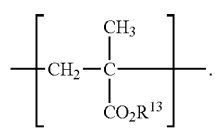

Non-limiting examples of this embodiment include:

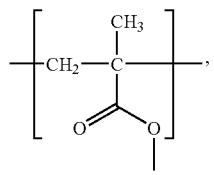 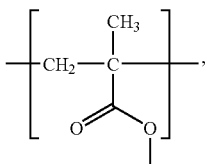

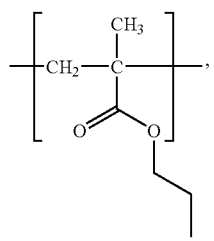 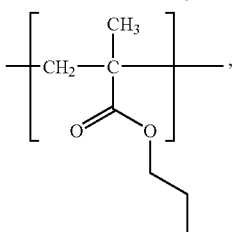

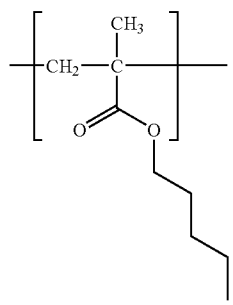 and

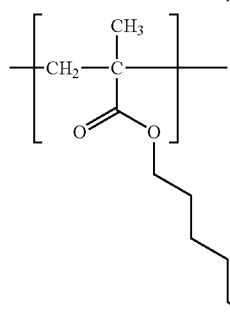

In a second aspect of the first category of backbone modifier units $R^{9a}$ and $R^{9b}$ are both hydrogen, $R^{10}$ is methyl ($C_1$), $R^{11}$ is an amide unit having the formula —C(O)NR$^{12a}$R$^{12b}$; wherein $R^{12a}$ is hydrogen, thereby providing a backbone modifier unit having the formula:

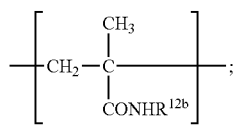

$R^{12b}$ is $C_1$-$C_{10}$ alkyl, inter alia, methyl ($C_1$), ethyl ($C_2$), n-propyl ($C_3$), n-butyl ($C_4$), n-pentyl ($C_5$), n-hexyl ($C_6$), and n-heptyl ($C_7$). Non-limiting examples of this embodiment include:

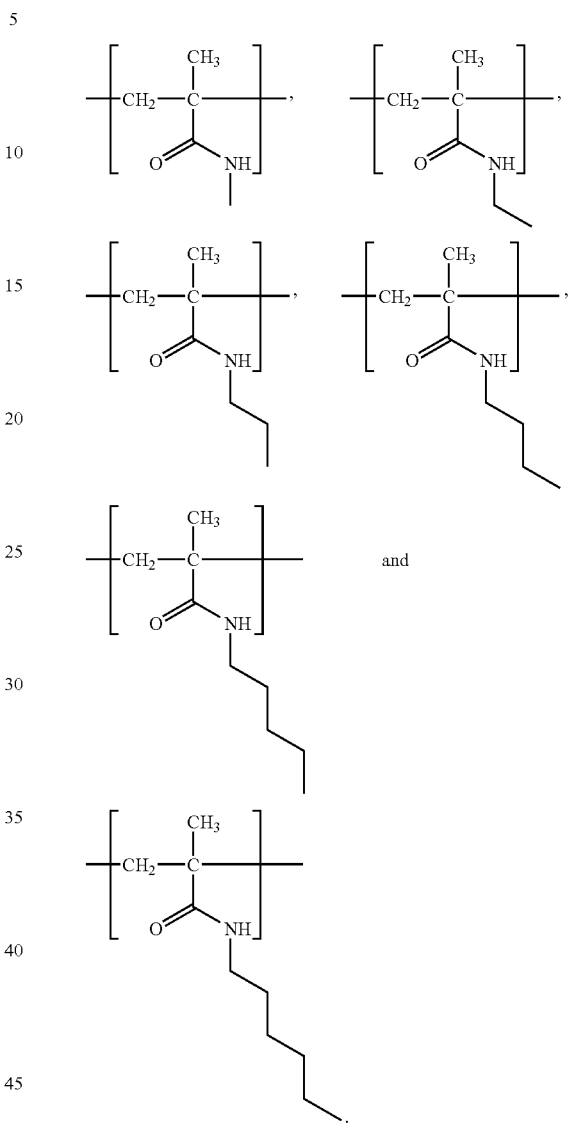

In a third aspect of the first category of backbone modifier units $R^{9a}$, $R^{9b}$, and $R^{10}$ are each hydrogen and $R^{11}$ is an ester unit having the formula —C(O)OR$^{13}$; providing a monomer having the formula:

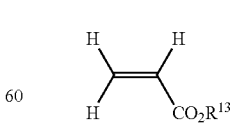

wherein $R^{13}$ is chosen from methyl ($C_1$), ethyl ($C_2$), n-propyl ($C_3$), n-butyl ($C_4$), n-pentyl ($C_5$), n-hexyl ($C_6$), and n-heptyl ($C_7$); thereby providing a backbone modifier unit having the formula:

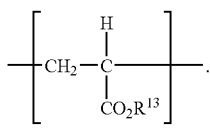

Non-limiting examples of this embodiment include:

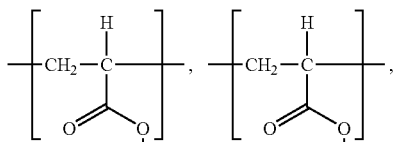

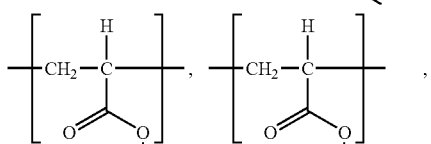

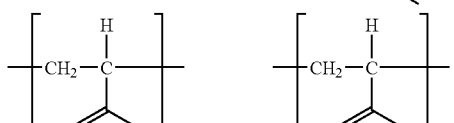

and

In a fourth aspect of the first category of backbone modifier units $R^{9a}$, $R^{9b}$, and $R^{10}$ are each hydrogen and, $R^{11}$ is an amide unit having the formula —C(O)NR$^{12a}$R$^{12b}$; wherein $R^{12a}$ is hydrogen, thereby providing a backbone modifier unit having the formula:

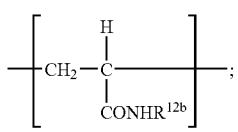

$R^{12b}$ is $C_1$-$C_{10}$ alkyl, inter alia, methyl ($C_1$), ethyl ($C_2$), n-propyl ($C_3$), n-butyl ($C_4$), n-pentyl ($C_5$), n-hexyl ($C_6$), and n-heptyl ($C_7$). Non-limiting examples of this embodiment include:

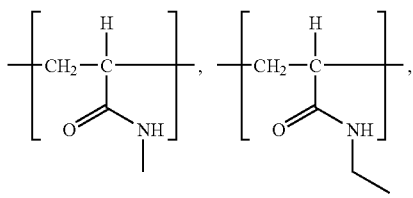

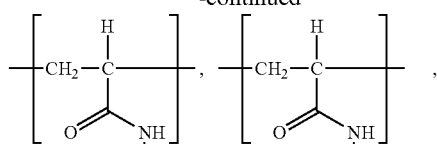

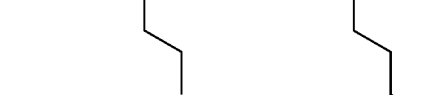

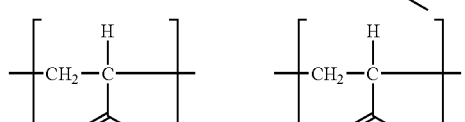

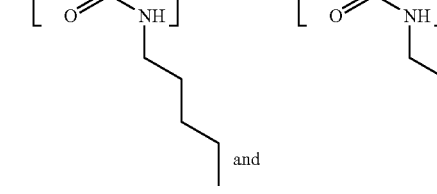

and

Crosslinking Units, XL

The crosslinking units of the present disclosure are units that are capable of forming a crosslink between two chains. In the first category of crosslinking units, the crosslink is formed between two crosslinking units on different chains, or sections of a single chain. In a second category, crosslinking may occur between a crosslinking unit having a reactive moiety and a functional group of a chain modifier unit.

The crosslinking units of the present disclosure have the formula:

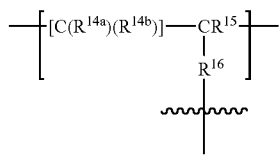

wherein $R^{14a}$, $R^{14b}$, and $R^{15}$ are each independently chosen from:
  i) hydrogen; and
  ii) $C_1$-$C_4$ alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$).

$R^{16}$ units serve to connect two polymer chains or separate sections of chains. In all the aspects of crosslinking units according to the present disclosure wherein two separate polymer chains are crosslinked by a crosslinking unit, the two units once joined, $R^{16}$ will have the formula:

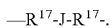

—$R^{17}$-J-$R^{17}$-.

Each $R^{17}$ is independently chosen from
  i) —(CH$_2$)$_p$C(O)(CH$_2$)$_q$—;
  ii) —(CH$_2$)$_p$C(O)O(CH$_2$)$_q$—;
  iii) —(CH$_2$)$_p$OC(O)(CH$_2$)$_q$—;
  iv) —(CH$_2$)$_p$NH(CH$_2$)$_q$—;
  v) —(CH$_2$)$_p$C(O)NH(CH$_2$)$_q$—;
  vi) —(CH$_2$)$_p$NHC(O)(CH$_2$)$_q$—;
  vii) —(CH$_2$)$_p$NHC(O)NH(CH$_2$)$_q$—;
  viii) —(CH$_2$)$_p$NHC(=NH)NH(CH$_2$)$_q$—; and
  ix) —(CH$_2$)$_p$—O—(CH$_2$)$_q$—;

the indices p and q have the value from 0 to 10; when p is 0 the —($CH_2$)— is absent; when q is 0 the —($CH_2$)— is absent;

J is a unit having the formula:

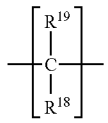

wherein $R^{18}$ and $R^{19}$ are each independently:
i) hydrogen;
ii) $C_1$-$C_{10}$ alkyl; or
iii) a unit capable of forming a crosslink to a third XL unit, the unit chosen from:
   a) —($CH_2$)$_r$C(O)H;
   b) —($CH_2$)$_r$C(O)OH;
   c) —($CH_2$)$_p$OC(O)H;
   d) —($CH_2$)$_r$$NH_2$;
   e) —($CH_2$)$_p$C(O)$NH_2$;
   f) —($CH_2$)$_r$NHC(O)H;
   g) —($CH_2$)$_r$NHC(O)$NH_2$;
   h) —($CH_2$)$_r$NHC(=NH)$NH_2$;
   i) —($CH_2$)$_r$C(=$CH_2$)$CH_3$;
   j) —($CH_2$)$_r$OH; and wherein the index r has the value from 0 to 10; when r is 0 the —($CH_2$)— is absent.

As with the HB and MOD units of the present disclosure, XL units are derived from monomers that react with HB and MOD units to form a polymer backbone. In a first category of XL units, there is a monomer that comprises two polymer chain forming units. The first aspect of the XL monomers relates to units having the formula:

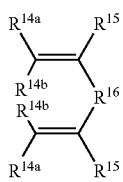

wherein each of the double bonds can independently react to form part of a separate polymer chain, $R^{16}$ is a unit that serves as a crosslinker. When the definition of $R^{16}$ is expanded, XL monomers of the first aspect of the first category have the formula:

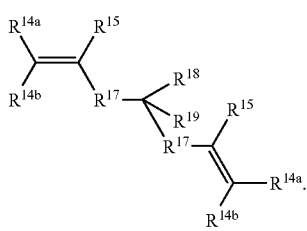

The following is a non-limiting example of a generic scheme that depicts the crosslinking of a XL unit according to the first category of crosslinking units. In this generic example both $R^{17}$ units are —C(O)O— units and J is a unit not capable of independently participating in polymer backbone formation. The generic crosslinking unit having the formula:

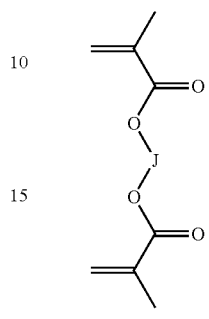

is reacted with a generic HB monomer and a generic MOD monomer to form a non-limiting example of a resultant generic polymer according to the scheme herein below.

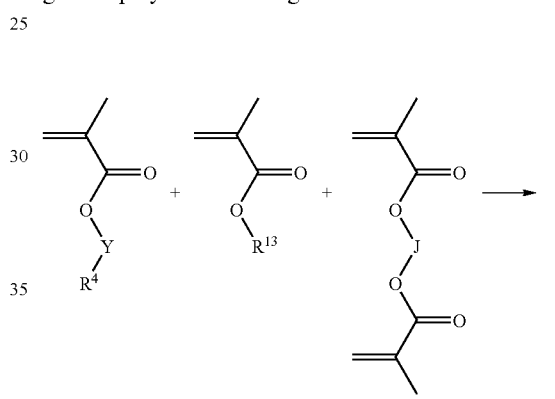

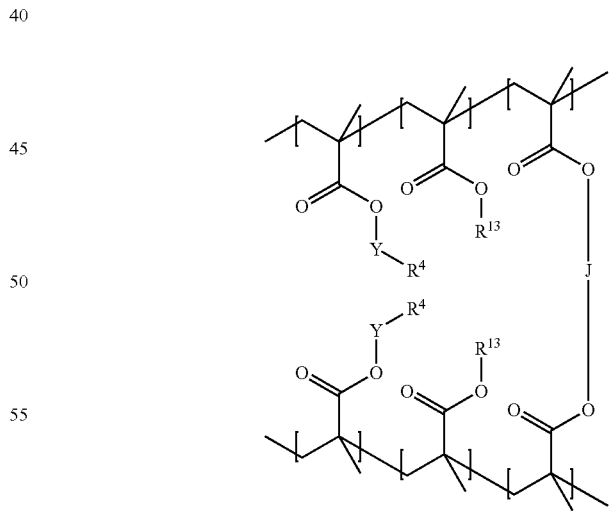

As discussed herein above, the formulator is not restricted to selecting only one monomer from each category for preparing the shape memory polymers of the present disclosure. For example, the scheme below depicts two different HB units being incorporated into a shape memory polymer of the present disclosure.

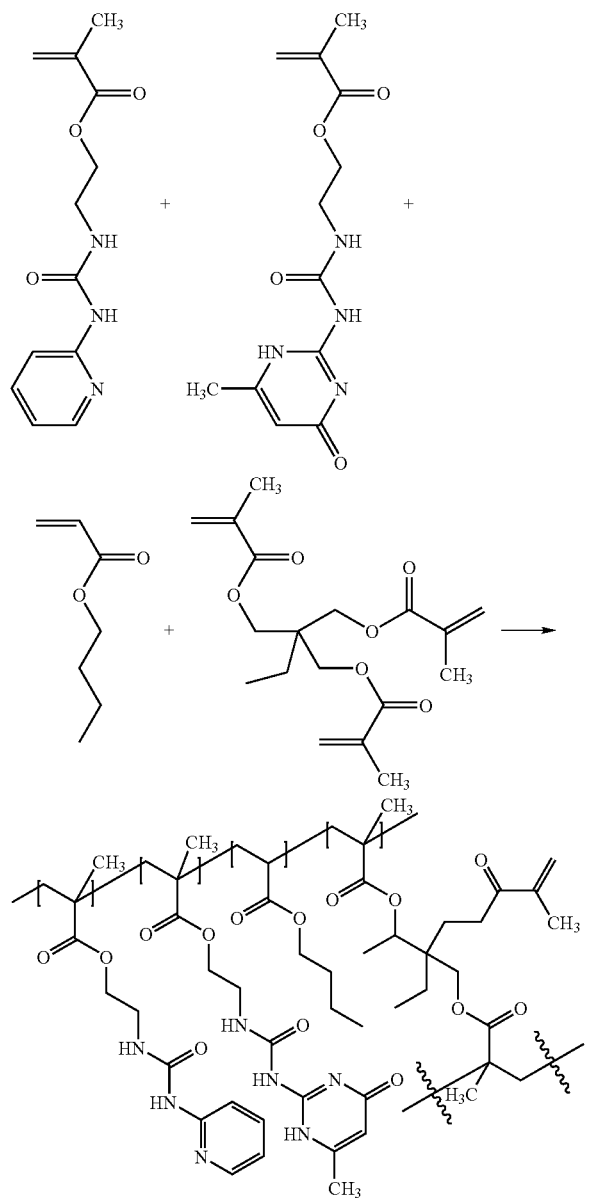

Likewise, any mixture of monomers can be used to formulate the shape memory polymers of the present disclosure.

The second category of XL units relates to monomers that comprise a unit that, once the polymer backbone is formed, contains a unit that can react with a reactive species that serves to form the final crosslink between two chains.

The XL monomers of the second category have the formula:

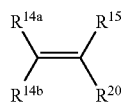

wherein $R^{20}$ is a unit comprising a reactive moiety capable of reaction with a reactive moiety of a J unit precursor, for example, a unit having the general formula:

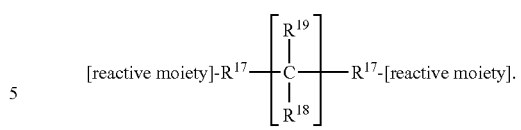

The reactive moieties that are suitable for undergoing reaction to form a crosslinked polymer chain include those that are capable of reacting under typical polymerization condition, inter alia, thermal, free radical, photo reaction, and cationic or anionic polymerization.

The artisan of ordinary skill will realize the reactive moieties of the polymer chain will in many instances be different from the reactive moiety that comprises the J unit precursor. As a non-limiting example, a bis-alcohol linking unit precursor can be reacted with a polymer chain comprising methacrylic acid units to form crosslinks as depicted herein below:

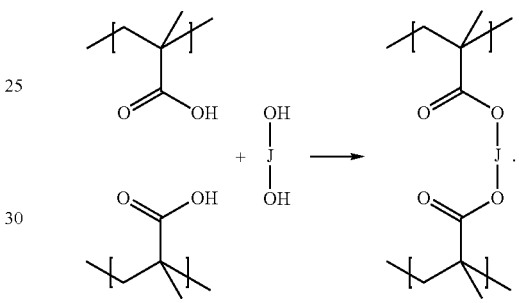

A further category of XL cross-linking units relates to photo crosslinking units, for example, units that are capable of forming crosslinks between two polymer chains when exposed to electromagnetic radiation, i.e., UV light. Shape Memory Polymers comprising photo crosslinking units can be cured by exposure to UV radiation. By varying the exposure time and light intensity the formulator can control the amount of crosslinking present.

The formulator can, by using this method of crosslinking, have an admixture of non-crosslinked copolymers that is a liquid and crosslink the polymer to form a solid or non-flowable crosslinked shape memory polymer. The formulator can make use of this embodiment by pouring the admixture of linear copolymers into a mold or other shape forming container, applying UV light, and thereby obtain the shape memory polymer in a desire form. Or in an alternative, a viscous solution of linear copolymers can be drawn out under UV radiation to form long threads or wires of shape memory polymers. An iteration of this embodiment is to draw out the shape memory polymers that can be crosslinked at two different UV wavelengths, wherein one wavelength is more reactive. In this way a partially crosslinked polymer can be drawn out at a first wavelength of UV radiation, formed into a desired configuration, then full crosslinked by UV radiation at a second wavelength.

One non-limiting example of photo crosslinking units is the monomer comprising a coumarin unit, the monomer having the formula:

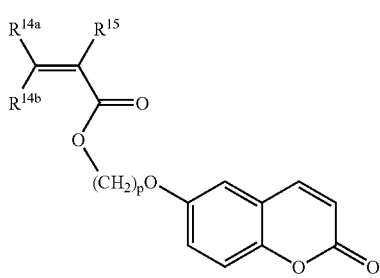

wherein $R^{14a}$, $R^{14b}$, $R^{15}$, and the index p are defined herein above.

The Shape Memory Polymers of the present disclosure are formed by reacting under suitable conditions, three types of monomers;

a) from about 0.5 to about 5 mol % of a monomer having the formula:

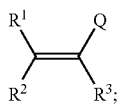

b) from about 90 to about 99 mol % of a monomer having the formula:

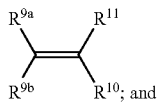

c)
  i) from about 0.5 to about 5 mol % of a monomer having the formula:

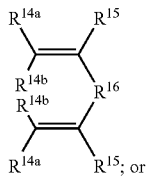

ii) from about 0.5 to about 5 mol % of a monomer having the formula:

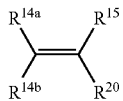

wherein $R^{20}$ is a reactive moiety capable of either:

a) reacting directly with another $R^{20}$ unit of a second polymer chain to form a $R^{16}$ crosslinking unit; or
b) two $R^{20}$ units from two polymer chains are capable of reacting with a molecule that comprises two reactive groups capable of reacting with both $R^{20}$ units to form a $R^{16}$ crosslinking unit.

A first category of polymers relates to reaction of:

a) from about 0.5 to about 5 mol % of one or more monomers having the formula:

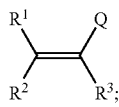

b) from about 90 to about 99 mol % of one or more monomers having the formula:

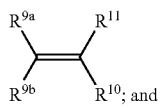

c) from about 0.5 to about 5 mol % of one or more monomers having the formula:

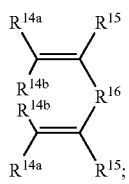

wherein each crosslinking monomer comprises a unit on two separate chains.

For example the generic monomer represented by the formula:

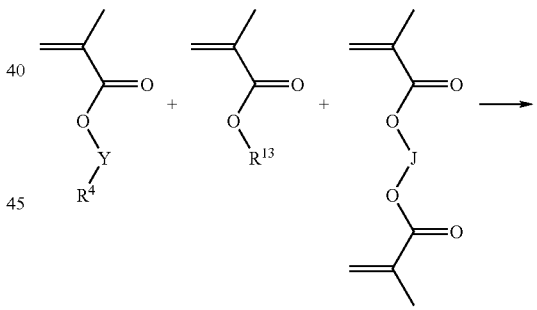

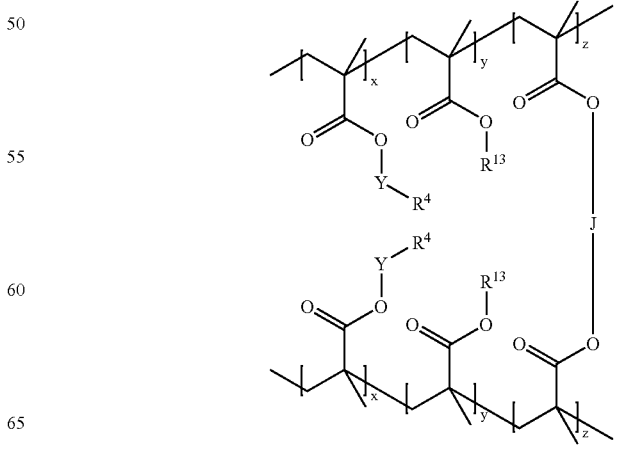

wherein the value for the index x (HB unit) is 5, the value for the index y (MOD unit) is 90, and the value for the index z (XL unit) is 5, as prepared by combining 5 mol % of a HB unit, 90 mol % of a MOD unit and 5 mol % of a crosslinking unit. This polymer would be represented by the following formula:

A second category of polymers relates to reaction of:
a) from about 0.5 to about 5 mol % of one or more monomers having the formula:

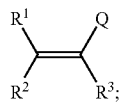

b) from about 90 to about 99 mol % of one or more monomers having the formula:

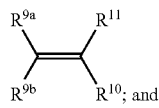

c) from about 0.5 to about 5 mol % of one or more monomers having the formula:

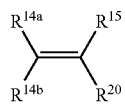

to form shape-memory polymer precursors in the form of linear polymeric chains that are then subsequently crosslinked, wherein $R^{20}$ comprises a reactive moiety that forms crosslinks after the polymer backbones are formed.

$R^{20}$ is a reactive moiety that is capable of reacting with an intermediate such that two $R^{20}$ units from two separate polymer chains react with the intermediate to form a crosslink between two polymer chains. A first iteration encompasses $R^{20}$ units chosen from:
  i) —C(O)O$R^{21}$;
  ii) —NCO; and
  iii) —N$_3$;
wherein $R^{21}$ is hydrogen or $C_1$-$C_4$ linear or branched alkyl.

In addition, the $R^{20}$ units described herein above have reactive units capable of reacting with a di-functional molecule to form a shape memory polymer according to the present disclosure, the di-functional molecule has the formula:

$R^{22}$ each is independently chosen from
  i) ClC(O)(CH$_2$)$_b$—;
  ii) Cl(CH$_2$)$_b$—;
  iii) H$_2$N(CH$_2$)$_b$—;
  iv) HOC(O)(CH$_2$)$_b$—;
  v) HO(CH$_2$)$_b$—;
  vi) OCN(CH$_2$)$_b$—; and
  vii) N$_3$(CH$_2$)$_b$—;
the index b is from 1 to 10.

A non-limiting example of this aspect includes shape memory polymer precursor chains having a —C(O)OH reactive moiety, for example:

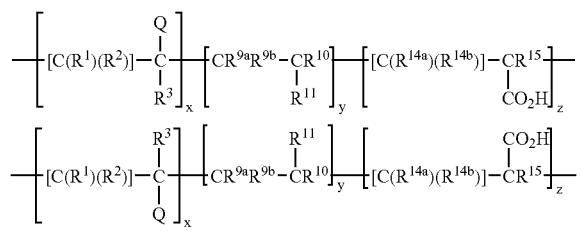

are treated with 1,8-dihydroxyoctane to form a shape memory polymer:

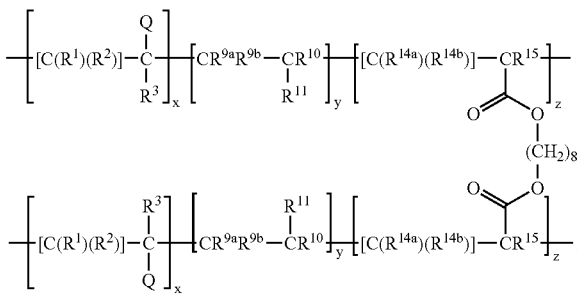

The following scheme shows the process for forming shape memory polymers of the present disclosure wherein the crosslinking is done after the polymer backbone is formed.

The first step involves forming linear polymer chains, for example, polymer chain formation produces a linear, crosslinkable backbone as depicted below, wherein RM represents a reactive moiety:

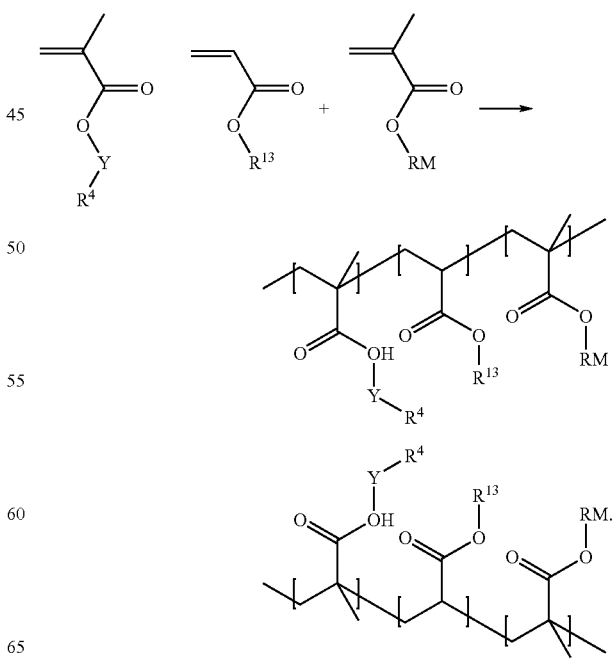

After backbone formation, the polymer is reacted with a compound that contains reactive moieties that can be used to crosslink the linear chains and thereby form a shape memory polymer.

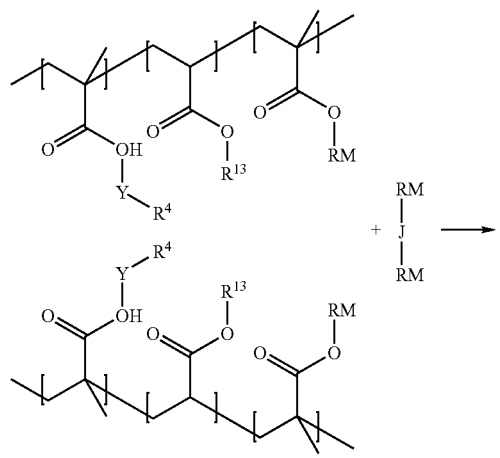

The following is a non-limiting generic example wherein a reactive moiety is added to a polymer backbone after which the polymer can be crosslinked by photo-crosslinking methods using UV radiation and a photoacid generator.

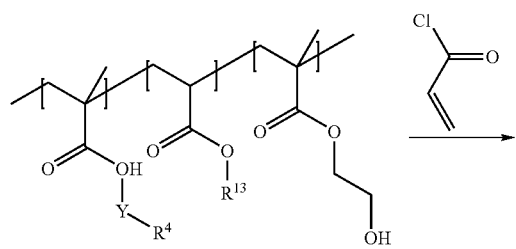

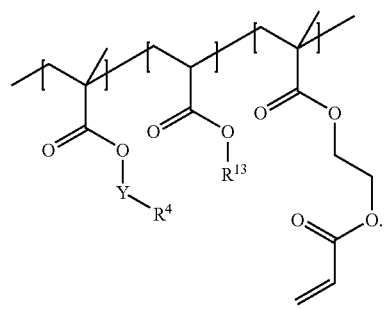

In a third category, the crosslinking monomer may comprise a reactive unit in such a manner that when after the polymer backbones are formed, the formulator may then crosslink the chains to form the final polymer as depicted in the following scheme:

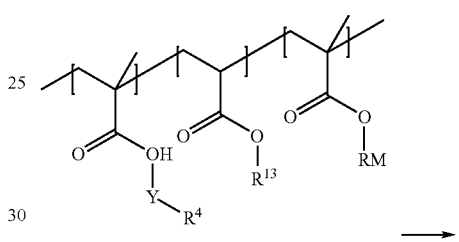

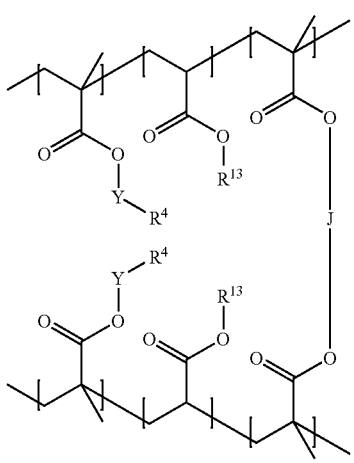

wherein the crosslinking may be accomplished by the use of a chemical reagent, or the formulator may take advantage of special reaction conditions that forms the crosslink.

The compounds that can react with the $R^{20}$ moieties and therefore be used to form the crosslinks, are any compounds capable of reaction with the units to form a J unit as defined herein above.

Non-limiting examples include:

i) $R^{20}$ units that are —C(O)OH reacting with di-alcohols having the formulae $HO(CH_2)_nOH$ wherein n is from 2 to 20, to form crosslinks having the formulae:

—C(O)O(CH_2)_nOC(O)—;

ii) $R^{20}$ units that are —C(O)OH reacting with di-amines having the formulae $H_2N(CH_2)_nNH_2$ wherein n is from 2 to 20, to form crosslinks having the formulae:

—C(O)NH(CH_2)_nNHC(O)—; and iii) $R^{20}$ units that are —NCO reacting with di-amines having the formulae $H_2N(CH_2)_nNH_2$ wherein n is from 2 to 20, to form crosslinks having the formulae:

—NHC(O)NH(CH_2)_nNHC(O)NH—.

PREPARATION OF POLYMERS

Schemes I-III and Examples 1-3 herein below provide examples of the preparation of a hydrogen bonding unit, HB, monomers according to the present disclosure.

Scheme I

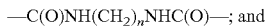
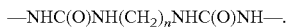

Example 1

3-Oxo-3-(pyridin-2-ylamino)propyl acrylate (2)

Preparation of 3-chloro-3-oxopropyl acrylate (1): 2-Carboxyethyl acrylate (1 eq.) is dissolved in $CH_2Cl_2$ and the solution is cooled in an ice bath. Thionyl chloride (1 eq.) is added dropwise and the mixture is allowed to warm to room temperature and stir for 4 hours. The solvent is removed under reduced pressure and the desired product is isolated by vacuum distillation.

Preparation of 3-oxo-3-(pyridin-2-ylamino)propyl acrylate (2): 3-Chloro-3-oxopropyl acrylate, 1, (1 eq.), 2-aminopyridine (1 eq.) and triethylamine (3 eq.) are dissolved in toluene at 0° C. A few crystals of hydroquinone is added to inhibit any polymerization side reactions. The solution is allowed to stir approximately 18 hours at a temperature from about 0° C. to room temperature. The solvent is removed under reduced pressure and the crude material purified over silica. For a more detailed account of this procedure See M. A. Diab, A. Z. El-Sonbati, A. A. El-S anabori, F. I. Taha, *Polymer Degrad. Stab.* 1989, 24, 51, included herein by reference.

Scheme II

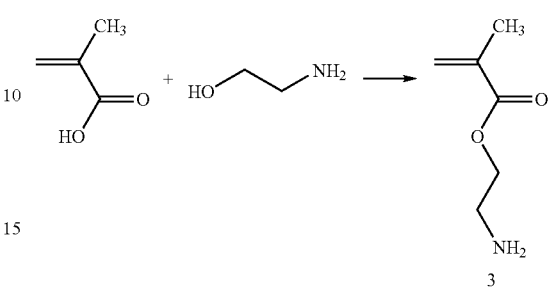
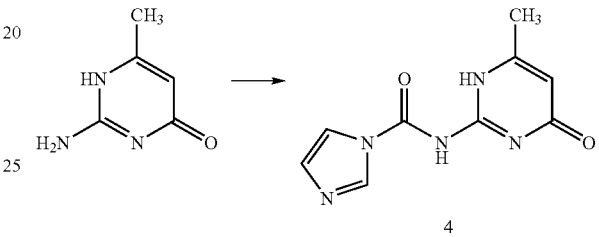
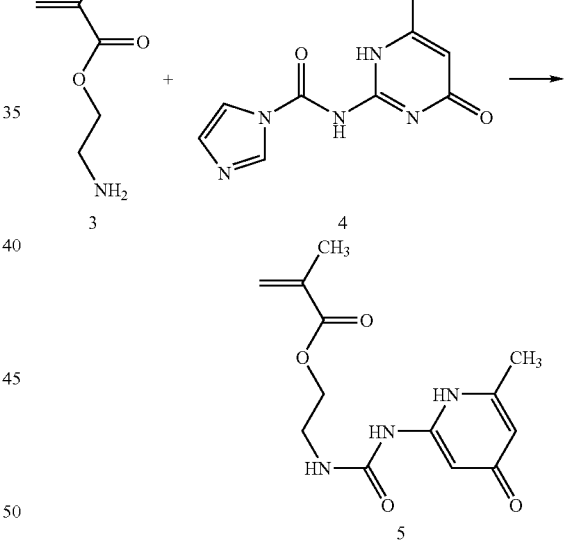

Example 2

2-[3-(6-Methyl-4-oxo-1,4-dihydropyridin-2-yl)ureido]ethyl methacrylate (5)

Preparation of 2-amino methacrylate (3): A mixture of ethanolamine hydrochloride (1 eq.), thionyl chloride (1 eq.) and a catalytic amount of Cu powder are heated together to 100° C. Over the next 2 hours methylacrylolyl chloride (2 eq.) is added after which the mixture is cooled to approximately 60° C. and ethyl acetate is added. Crystals may begin to form as the solution cools. The crude product is recrystallized from ethyl acetate/isopropanol to afford the desired product. For a more detailed account of this procedure See J. M. Geurts, C. M. Gottgens, M. A. I. Van Graefschepe, et al., *J. of Applied Polymer Science,* 2001, 80, 1401 included herein by reference.

Preparation of N-(6-methyl-4-oxo-1,4-dihydropyrimidin-2-yl)-1H-imidazole-1-carboxamide (4): A mixture of 6-methylisocytosine (1 eq.) and carbonyldiimidazole (1.5 eq.) were combined in dimethylsulfoxide (DMSO) and the solution was stirred at 60° C. for 2 hours. The mixture was cooled to about room temperature and acetone added after which the desired product precipitated as a white powder that was collected by filtration. The procedure of A. T. Cate, P. Y. W. Dankers, H. Kooijman, A. L. Spek, R. P. Sijbesma, and E. W. Meijer, *J. of Am. Chem. Soc.,* 2003, 125, 6860 was followed for this step. The product can be used without further purification.

Preparation of 2-[3-(6-methyl-4-oxo-1,4-dihydropyridin-2-yl)ureido]ethyl methacrylate (5): To a solution of 2-amino methacrylate hydrochloride, 3, (1 eq.) and triethylamine (1 eq.) in chloroform (30 mL) is added N-(6-methyl-4-oxo-1,4-dihydropyrimidin-2-yl)-1H-imidazole-1-carboxamide, 4, (1 eq.). The reaction mixture is stirred for 4 hours at 50° C. and the solvent is removed under reduced pressure. The residue is purified over silica, and the product was obtained by precipitation in methanol. For a more detailed description See A. T. Cate, P. Y. W. Dankers, H. Kooijman, A. L. Spek, R. P. Sijbesma, and E. W. Meijer, *J. of Am. Chem. Soc.,* 2003, 125, 6860 include herein by reference.

Scheme III

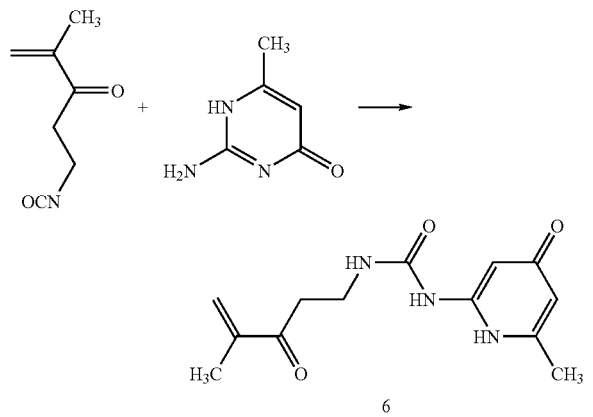

Reagents and conditions: (a) DMSO; 130° C., 1 min.

Example 3

1-(4-Methyl-3-oxopeny-4-enyl)-3-(6-methyl-4-oxo-1,4-dihydropyridin-2-yl)urea [UPy-EA] (6)

Preparation of 1-(4-Methyl-3-oxopeny-4-enyl)-3-(6-methyl-4-oxo-1,4-dihydropyridin-2-yl)urea [UPy-EA] (6): The procedure of K. Yamauchi; J. R. Lizotte; T. E. Long. *Macromolecules* 2003, 36, 1083-1088, included herein by reference, was followed for the preparation of the title compound, that is summarized herein below. 6-Methylisocytosine (1.25 g, 10.0 mmol) was dissolved in DMSO (10 mL) at 130° C., 2-isocyanatoethyl methacrylate (available from Aldrich Chemical Co.) (1.70 g, 11.0 mmol) was added. In less than 1 min, the mixture was quenched by a water bath. The precipitated white solid was filtered and washed with hexane. Yield ~70%.

The following Scheme IV and Example 4 illustrate the preparation of a shape memory polymer according to the present disclosure.

Scheme IV

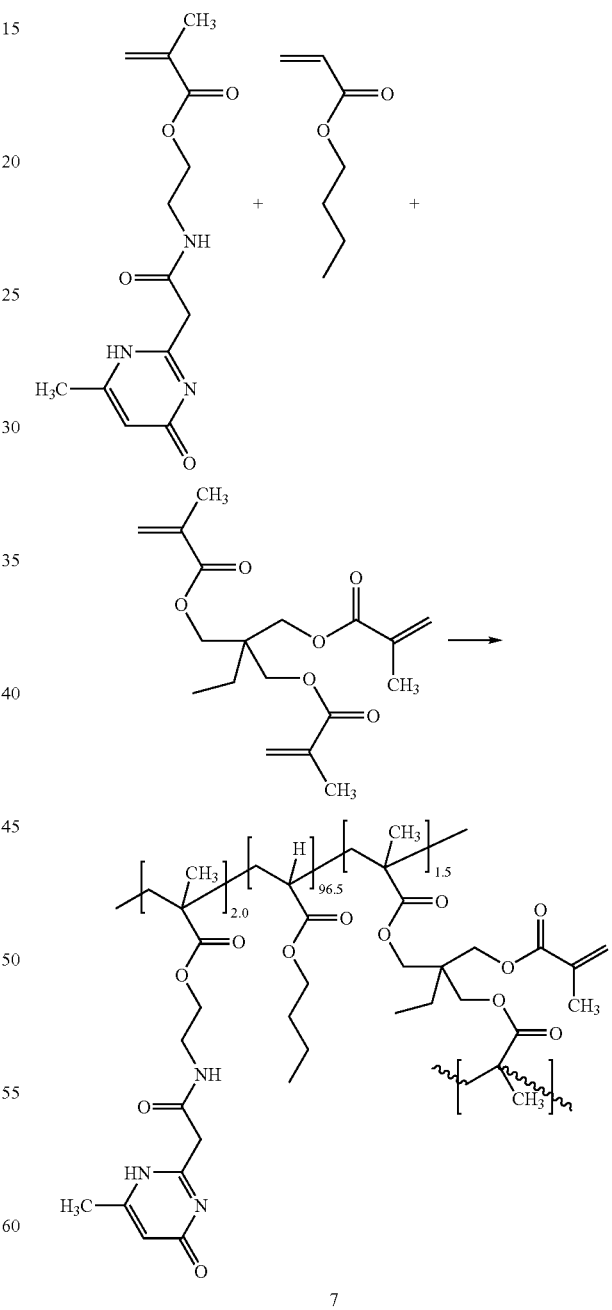

Reactions and conditions (a) : AIBN, NMP; 65° C. 12 hr.

Example 4

[Butyl acrylate]$_{96.5}$[trimethylolpropane trimethacrylate]$_{1.5}$-[UPy-EA]$_{2.0}$ Preparation of [Butyl acrylate]$_{96.5}$-[trimethylolpropane trimethacrylate]$_{1.5}$[UPy-EA]$_{2.0}$ (7): To a reaction vessel was charged butyl acrylate (96.5 mol %), trimethylol-propane trimethacrylate (1.5 mol %), and 1-(4-Methyl-3-oxopeny-4-enyl)-3-(6-methyl-4-oxo-1,4-dihydropyridin-2-yl)urea, 7, (2.0 mol %) were combined with N-methyl-pyrrolidinone (50% by wt.) at room temperature. Nitrogen gas was bubbled through the reaction mixture for 30 minutes. Azobisisobutylnitrile [AIBN] (1.0 mmol) was added and the reaction mixture injected onto a Petri dish inside a custom built gas-tight, bell-jar apparatus. The temperature of the reaction was controlled at 65° C. while the reaction apparatus was continuously purged with nitrogen during the course of the reaction. After 12 hours the reaction apparatus is cooled and the resulting shape memory polymer is dried for 48 hours.

The following is an example of another iteration of the polymer outlined in Scheme IV.

Example 5

[Butyl acrylate]$_{97.5}$[trimethylolpropane trimethacrylate]$_{1.5}$ [UPy-EA]$_{1.0}$ Preparation of [Butyl acrylate]$_{96.5}$-[trimethylolpropane trimethacrylate]$_{1.5}$[UPy-EA]$_{2.0}$ (7): To a reaction vessel was charged butyl acrylate (97.5 mol %), trimethylol-propane trimethacrylate (1.5 mol %), and 1-(4-Methyl-3-oxopeny-4-enyl)-3-(6-methyl-4-oxo-1,4-dihydropyridin-2-yl)urea, 7, (1.0 mol %) were combined with N-methyl-pyrrolidinone (50% by wt.) at room temperature. Nitrogen gas was bubbled through the reaction mixture for 30 minutes. Azobisisobutylnitrile [AIBN] (1.0 mmol) was added and the reaction mixture injected onto a Petri dish inside a custom built gas-tight, bell-jar apparatus. The temperature of the reaction was controlled at 65° C. while the reaction apparatus was continuously purged with nitrogen during the course of the reaction. After 12 hours the reaction apparatus is cooled and the resulting shape memory polymer is dried for 48 hours.

The following are non-limiting examples of shape memory polymers according to the present disclosure.

| 1$^{st}$ Iteration | | | |
|---|---|---|---|
| HB monomer | Q moiety | | R$^4$ |
| CH$_2$=C(CH$_3$)Q | —CO$_2$(CH$_2$)$_2$NHC(O)NHR$^4$ | | 6-methylpyrimidin-4-(1H)-on-2-yl |
| MOD monomer | R$^{11}$ | | R$^{13}$ |
| CH$_2$=CHR$^{11}$ | —CO$_2$R$^{13}$ | | n-butyl |
| XL monomer | R$^{16}$ | | J |
| CH$_2$=C(CH$_3$)R$^{16}$ | —C(O)OCH$_2$JCH$_2$OC(O)— | | —C(C$_2$H$_5$)[CH$_2$O$_2$CC(=CH$_2$)CH$_3$]— |
| No. | MOD mol % | HB mol % | XL mol % |
| 1 | 96.5 | 1.0 | 2.5 |
| 2 | 97.0 | 1.0 | 2.0 |
| 3 | 96.5 | 2.0 | 1.5 |
| 4 | 97.0 | 2.0 | 1.0 |

| 2$^{nd}$ Iteration | | | |
|---|---|---|---|
| HB monomer | Q moiety | | R$^4$ |
| CH$_2$=C(CH$_3$)Q | —CO$_2$(CH$_2$)$_3$NHC(O)NHR$^4$ | | 6-methylpyrimidin-4-(1H)-on-2-yl |
| MOD monomer | R$^{11}$ | | R$^{13}$ |
| CH$_2$=CHR$^{11}$ | —CO$_2$R$^{13}$ | | n-butyl |
| XL monomer | R$^{16}$ | | J |
| CH$_2$=C(CH$_3$)R$^{16}$ | —C(O)OCH$_2$JCH$_2$OC(O)— | | —C(C$_2$H$_5$)[CH$_2$O$_2$CC(=CH$_2$)CH$_3$]— |
| No. | MOD mol % | HB mol % | XL mol % |
| 5 | 96.5 | 1.0 | 2.5 |
| 6 | 97.0 | 1.0 | 2.0 |
| 7 | 96.5 | 2.0 | 1.5 |
| 8 | 97.0 | 2.0 | 1.0 |

| 3rd Iteration | | |
|---|---|---|
| HB monomer | Q moiety | $R^4$ |
| $CH_2=C(CH_3)Q$ | $-CO_2(CH_2)_4C(O)NHR^4$ | 6-methylpyrimidin-4-(1H)-on-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 9 | 96.5 | 1.0 | 2.5 |
| 10 | 97.0 | 1.0 | 2.0 |
| 11 | 96.5 | 2.0 | 1.5 |
| 12 | 97.0 | 2.0 | 1.0 |

| 4th Iteration | | |
|---|---|---|
| HB monomer | Q moiety | $R^4$ |
| $CH_2=C(CH_3)Q$ | $-CO_2(CH_2)_2C(O)NHR^4$ | 6-methylpyrimidin-4-(1H)-on-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 13 | 96.5 | 1.0 | 2.5 |
| 14 | 97.0 | 1.0 | 2.0 |
| 15 | 96.5 | 2.0 | 1.5 |
| 16 | 97.0 | 2.0 | 1.0 |

| 5th Iteration | | |
|---|---|---|
| HB monomer | Q moiety | $R^4$ |
| $CH_2=C(CH_3)Q$ | $-CO_2(CH_2)_2NHC(O)NHR^4$ | pyridin-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |

| No. | MOD mol % | HB mol % | XL mol % |
|---|---|---|---|
| 17 | 96.5 | 1.0 | 2.5 |
| 18 | 97.0 | 1.0 | 2.0 |
| 19 | 96.5 | 2.0 | 1.5 |
| 20 | 97.0 | 2.0 | 1.0 |

| 6th Iteration | | |
| --- | --- | --- |
| HB monomer | Q moiety | $R^4$ |
| $CH_2=C(CH_3)Q$ | $-CO_2(CH_2)_3NHC(O)NHR^4$ | pyridine-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |
| No. | MOD mol % | HB mol % | XL mol % |
| --- | --- | --- | --- |
| 21 | 96.5 | 1.0 | 2.5 |
| 22 | 97.0 | 1.0 | 2.0 |
| 23 | 96.5 | 2.0 | 1.5 |
| 24 | 97.0 | 2.0 | 1.0 |

| 7th Iteration | | |
| --- | --- | --- |
| HB monomer | Q moiety | $R^4$ |
| $CH_2=C(CH_3)Q$ | $-CO_2(CH_2)_4C(O)NHR^4$ | pyridin-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |
| No. | MOD mol % | HB mol % | XL mol % |
| --- | --- | --- | --- |
| 25 | 96.5 | 1.0 | 2.5 |
| 26 | 97.0 | 1.0 | 2.0 |
| 27 | 96.5 | 2.0 | 1.5 |
| 28 | 97.0 | 2.0 | 1.0 |

| 8th Iteration | | |
| --- | --- | --- |
| HB monomer | Q moiety | $R^4$ |
| $CH_2=C(CH_3)Q$ | $-CO_2(CH_2)_2C(O)NHR^4$ | pyridin-2-yl |
| MOD monomer | $R^{11}$ | $R^{13}$ |
| $CH_2=CHR^{11}$ | $-CO_2R^{13}$ | n-butyl |
| XL monomer | $R^{16}$ | J |
| $CH_2=C(CH_3)R^{16}$ | $-C(O)OCH_2JCH_2OC(O)-$ | $-C(C_2H_5)[CH_2O_2CC(=CH_2)CH_3]-$ |
| No. | MOD mol % | HB mol % | XL mol % |
| --- | --- | --- | --- |
| 29 | 96.5 | 1.0 | 2.5 |
| 30 | 97.0 | 1.0 | 2.0 |
| 31 | 96.5 | 2.0 | 1.5 |
| 32 | 97.0 | 2.0 | 1.0 |

Figure 6:
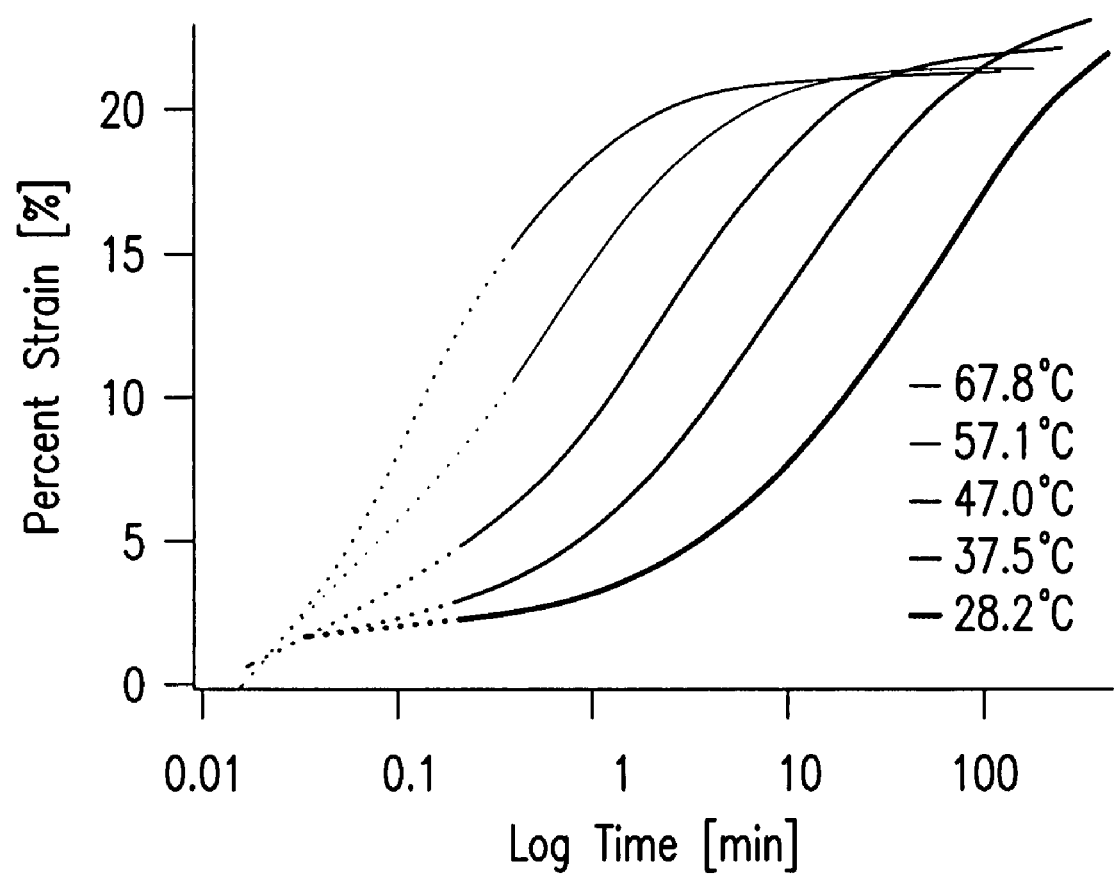
FIG. 6. depicts the percent strain of the polymer of Example 4 at various temperatures over time.

Thermal-mechanical analysis experiments were conducted on the Shape Memory Polymer of Example 4. Experimental data showing typical shape memory responses are shown in FIG. 5. On the left, the solid line indicates percent strain. The sample is initially deformed (approximately 22% strain) at 60° C. using a 50 mN (10 kPa) load. While under load, the temperature (dotted line) is reduced to approximately 5° C., and then the load (dotted line) is removed. The sample is "pinned" in its temporary shape, but slowly recovers. The rate of recovery is accelerated by increasing temperature. Polymers without associating side-groups behave as nearly ideal elastomers. The number of associating side groups present in the polymer influences the time-temperature dependence of shape recovery. To further illustrate this fact, the creep compliance of this polymer is in FIG. 6. The sample is isothermally loaded with a 50 mN load at various temperatures. The data can be collapsed onto a master curve using an appropriate shift factor. These data demonstrate an elastomeric network that is functionalized with a reversibly associating side-group whereby the material has no crystallinity and is well above its glass transition. The architecture of the presently disclosed polymers enables precise fine-tuning of physical properties.

When the disclosed polymers are elastically deformed at a shape memory temperature $T_{SM}$ and subsequently lowered to a shape memory temperature, $T_F$, and the method by which the polymer is elastically deformation is removed, the polymer returns to its original shape at a recovery rate, $R_{REC}$, that is inversely related to the difference in the temperature, $\Delta T_{DEF}$, wherein $\Delta T_{DEF} = T_{SM} - T_F$.

The recovery rate of the shape memory polymers disclosed herein are not always linear over time or over temperature. The formulator can take advantage of this differential recovery rate. In one instance, the formulator can utilize an initial slow shape recovery for embodiments wherein the user needs some amount of time to position and/or adjust the position of the distended polymer. Likewise, in another embodiment, an initial quick recovery rate will allow the polymer to function, for example, in controlling the bleeding of an artery, whereas the slower late recovery rate allows the user to finely adjust the position of the polymer or to cut away unused or unnecessary portions.

The percent strain recovery, $\Delta_{REC}$, at any point along the recovery curve is defined herein as:

$$\Delta_{STRAIN} = S_i - S_t$$

wherein $S_i$ is the initial percent strain and $S_t$ is the percent strain at time t. Using the solid line curve in FIG. 5, the initial percent strain, $S_i$, is approximately 22% at 50 minutes and the percent strain at about 120 minutes, $S_{120}$, is approximately 17%. Therefore the $\Delta_{STRAIN}$ is 5% at 120 minutes. This corresponds to the polymer recovering approximately 23% of its original form in 70 minutes. Therefore, the rate of recovery over this portion of the curve is approximately 0.33%/minute. Considering the balance of the curve from time 120 minutes to about 140 minutes, the recovery rate over this portion of the curve is approximately 3.9%/minute. The formulator can take advantage of this differential rate of recovery. By manipulation of the polymer backbone and number of crosslinking units, the formulator can adjust the recovery rate to suit any particular application.

The shape memory polymers of the present disclosure have an overall recovery rate, $R_{REC}$, of from about 0.001%/minute to about 100%/minute. One embodiment of the polymers disclosed herein have an overall $R_{REC}$ of from about 0.05%/minute to about 20%/minute. In another embodiment, the polymers disclosed herein have a $R_{REC}$ of from about 0.1%/minute to about 10%/minute. In a further embodiment, the polymers disclosed herein have a $R_{REC}$ of from about 0.5%/minute to about 10%/minute. In still another embodiment, the polymers disclosed herein have a $R_{REC}$ of from about 1%/minute to about 20%/minute. In yet another embodiment, the polymers disclosed herein have a $R_{REC}$ of from about 5%/minute to about 20%/minute.

The shape memory polymers can also have overall recovery rates that include variable recovery rates for portions of the recovery cycle, for example a portion of the overall recovery rate that is slower than the overall recovery rate. In one embodiment of a slower recovery rate, the recovery rate, $R_{REC}$, over at least 10% of the recovery curve, is from about 0.001%/minute to about 5%/minute. In another embodiment of a slower recovery rate, the recovery rate, $R_{REC}$, over at least 10% of the recovery curve, is from about 0.01%/minute to about 1%/minute. In yet another embodiment of a slower recovery rate, the recovery rate, $R_{REC}$, over at least 10% of the recovery curve, is from about 0.1%/minute to about 1%/minute.

The shape memory polymers can also have a faster variable recovery rates for portions of the recovery cycle, for example a portion of the overall recovery rate that is faster than the overall recovery rate. In one embodiment of a faster recovery rate, the recovery rate, $R_{REC}$, over at least 10% of the recovery curve, is from about 1%/minute to about 100%/minute. In another embodiment of a faster recovery rate, the recovery rate, $R_{REC}$, over at least 10% of the recovery curve, is from about 5%/minute to about 75%/minute. In yet another embodiment of a faster recovery rate, the recovery rate, $R_{REC}$, over at least 10% of the recovery curve, is from about 10%/minute to about 50%/minute.

The shape memory polymers of the present invention can be used to form biocompatible devices. For example, shape memory polymers can be used in forming hearing protection. An ear plug formed from a SMP can be deformed at room temperature to over 100% strain, and it returns to its original shape on the order of several minutes after insertion into the ear thereby closing the ear channel and offering a tight, sound reducing ear plug.

Because the human body has a relatively constant temperature, SMP's that have a specific form at body temperature can be elastically deformed at a higher temperature, inserted into the human body, and then returned to their original shape or configuration once equilibrated with the body's temperature. Non-limiting examples of medical uses include stents, sutures, vascular compresses, vascular clips, and the like.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polymer having the formula:

—[HB]$_x$-[MOD]$_y$-[XL]$_z$- comprising:
   i) hydrogen bonding units, HB, having at least one hydrogen bond donor moiety and at least one hydrogen bond acceptor moiety;
   ii) backbone modifier units, MOD; and
   iii) crosslinking units, XL, that are capable of forming one or more crosslinks; the indices x, y, and z represent the mole fraction of each unit, the index x is from about 0.1 to about 20, the index y is from about 75 to about 99.8, and the index z is from about 0.1 to about 5;
   wherein the polymer is characterized by having a shape memory temperature, $T_{SM}$, such that the polymer can be elastically deformed at the shape memory temperature, and subsequently lowered to a shape memory freezing temperature, $T_F$, and the method of elastic deformation is removed, the polymer will return to its original shape with a rate slower than the rate observed if the method of mechanical elastic deformation were removed at $T_{SM}$; provided the shape memory freezing temperature $T_F$ is above the glass transition, $T_G$, of the polymer, and provided the polymer is in the amorphous state at $T_F$.

2. A polymer according to claim 1, wherein when the polymer is elastically deformed at a shape memory temperature $T_{SM}$ and subsequently lowered to a shape memory temperature, $T_F$, and the method by which the polymer is elastically deformation is removed, the polymer returns to its original shape at an overall recovery rate, $R_{REC}$, and wherein further the recovery rate is inversely related to the difference in the temperature, $\Delta T_{DEF}$, wherein $\Delta T_{DEF} = T_{SM} - T_F$.

3. A polymer according to claim 2, wherein the overall $R_{REC}$ is from about 0.001%/minute to about 100%/minute.

4. A polymer according to claim 3, wherein the overall $R_{REC}$ is from about 0.05%/minute to about 20%/minute.

5. A polymer according to claim 4, wherein the overall $R_{REC}$ is from about 0.1%/minute to about 10%/minute.

6. A polymer according to claim 5, wherein the overall $R_{REC}$ is from about 0.5%/minute to about 10%/minute.

7. A polymer according to claim 6, wherein the overall $R_{REC}$ is from about 1%/minute to about 20%/minute.

8. A polymer according to claim 7, wherein the overall $R_{REC}$ is from about 5%/minute to about 20%/minute.

9. A polymer according to claim 2, wherein the overall recovery rate includes a variable recovery rate over at least 10% of the recovery rate that is from about 0.001%/minute to about 5%/minute.

10. A polymer according to claim 9, wherein the variable recovery rate is from about 0.01%/minute to about 1%/minute.

11. A polymer according to claim 10, wherein the variable recovery rate is from about 0.1%/minute to about 1%/minute.

12. A polymer according to claim 2, wherein the overall recovery rate includes a variable recovery rate over at least 10% of the recovery rate that is from about 1%/minute to about 100%/minute.

13. A polymer according to claim 12, wherein the overall recovery rate includes a variable recovery rate over at least 10% of the recovery rate that is from about 5%/minute to about 75%/minute.

14. A polymer according to claim 13, wherein the overall recovery rate includes a variable recovery rate over at least 10% of the recovery rate that is from about 10%/minute to about 50%/minute.

15. A polymer according to claim 1, wherein the HB unit has the formula:

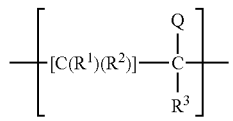

wherein each $R_1$ and $R_2$ is independently chosen from:
i) hydrogen;
ii) $C_1$-$C_6$ alkyl;
iii) halogen;
iv) cyano; and
v) phenyl;
$R_3$ is chosen from:
i) hydrogen; and
ii) $C_1$-$C_6$ alkyl; and Q is a unit having at least one hydrogen bond donor moiety or at least one hydrogen bond acceptor moiety;
the index m is from 1 to 4.

16. A polymer according to claim 15, wherein Q has the formula:

wherein when the index i is equal to 1, the linking group L is present, when the index i is equal to 0 the linking unit is absent;
L is a linking unit having the formula:

W and Z are each independently chosen from:
i) —C(O)—;
ii) —C(O)O—;
iii) —OC(O)—;
iv) —NH—;
v) —C(O)NH—;
vi) —NHC(O)—;
vii) —NHC(O)NH—;
viii) —NHC(=NH)NH—; and
ix) —O—;
the indices h and k are independently equal to 0 or 1; when h is 0 the W unit is absent, when h is 1 the W unit is present; when k is 0 the W unit is absent, when k is 1 the W unit is present;
Y is a unit having one or more units chosen from:
i) —$(CR^{5a}R^{5b})_s$—;
ii) —$[(CR^{5a}R^{5b})_v(CR^{5a'}R^{5b'})_u]_w$—;
iii) —$[(CR^{5a}R^{5b})_tO]_w$—; or
iv) —$[(CR^{5a}R^{5b})_tO]_w(CR^{5a}R^{5b})_s$—;
each $R^{5a}$ and $R^{5b}$ is independently chosen from:
i) hydrogen; or
ii) $C_1$-$C_4$ alkyl;
$R^{5a'}$ and $R^{5b'}$ are each independently $C_1$-$C_4$ alkyl;
the index j is 0 or 1; when j is equal to 0 the Y unit is absent, when j is equal to 1 the Y unit is present; the index s is from 0 to 10, the index t is from 2 to 10, the index u is from 1 to 10, the index v is from 1 to 10, the index w is from 1 to 10;
$R^4$ is a unit chosen from:
i) hydrogen;
ii) a substituted carbocyclic ring;
iii) a substituted aryl ring;
iv) a substituted or unsubstituted heterocyclic ring; or
v) a substituted of unsubstituted heteroaryl ring;
the substitution is a moiety capable of being a hydrogen bond donor or a hydrogen bond acceptor.

17. A polymer according to claim 16, wherein $R^4$ is a substituted or unsubstituted $C_3$ or $C_4$ heterocyclic or heteroaryl ring chosen from:
i) a pyrrolidinyl ring having the formula;

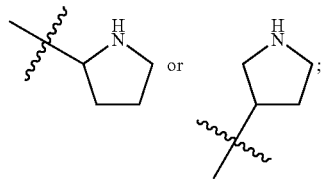

ii) a pyrrolyl ring having the formula:

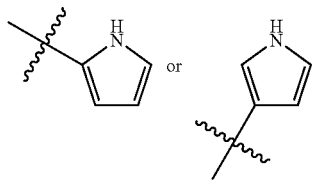

iii) a 4,5-dihydroimidazolyl ring having the formula:

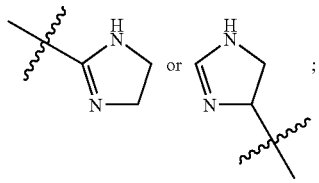

iv) an imidazolyl ring having the formula:

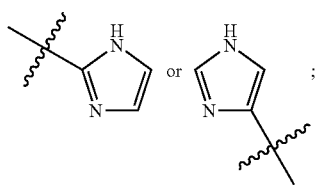

v) a pyrrolidinonyl ring having the formula:

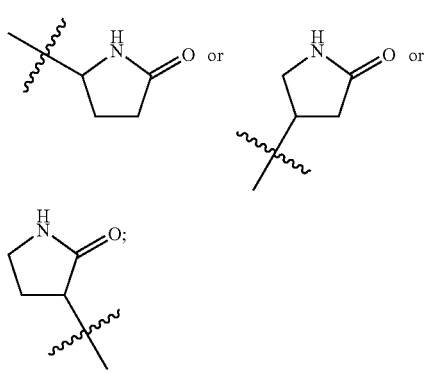

vi) an imidazolidinonyl ring having the formula:

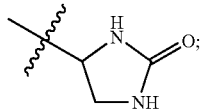

vii) an imidazol-2-only ring having the formula:

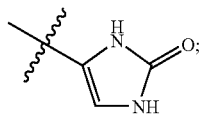

viii) an oxazolyl ring having the formula:

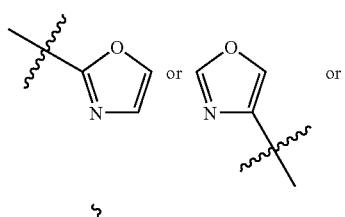

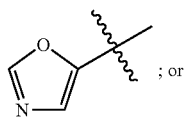

ix) a furanyl ring having the formula:

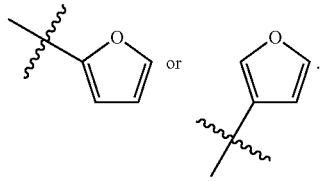

18. A polymer according to claim 16, wherein $R^4$ is a substituted, or unsubstituted $C_3$, $C_4$, or $C_5$ heterocyclic or heteroaryl ring chosen from:

i) a morpholinyl ring having the formula:

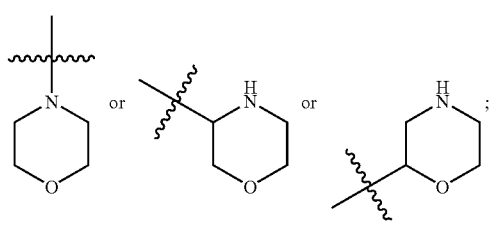

ii) a piperidinyl ring having the formula:

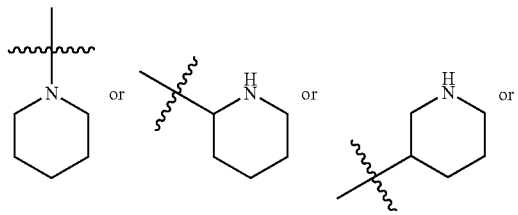

-continued
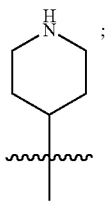
iii) a pyridinyl ring having the formula:
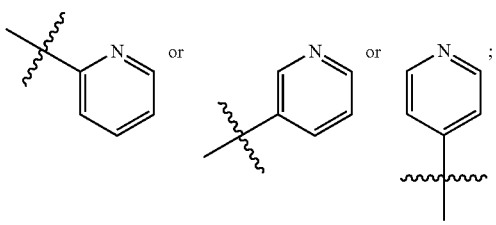
iv) a piperazinyl ring having the formula:
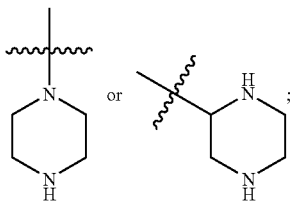
v) a ketopiperazinyl ring having the formula:
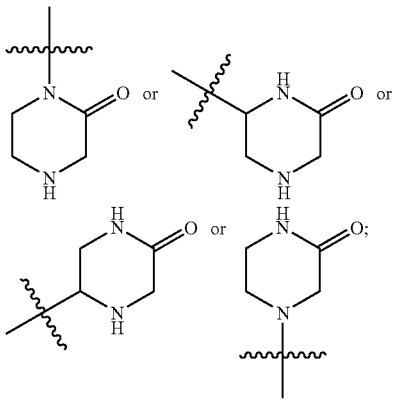
vi) a dihydropyrazin2-onyl ring having the formula:
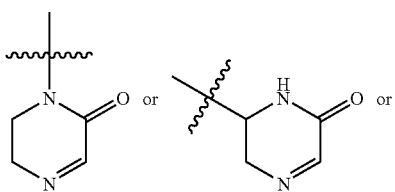
-continued
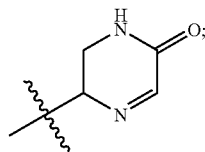
vii) a pyrazin2-onyl ring having the formula:
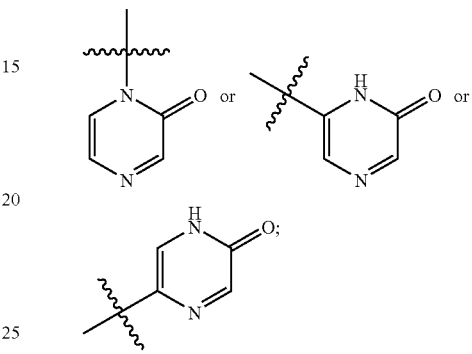
viii) dihydropyrimidin-4-onyl having the formula:
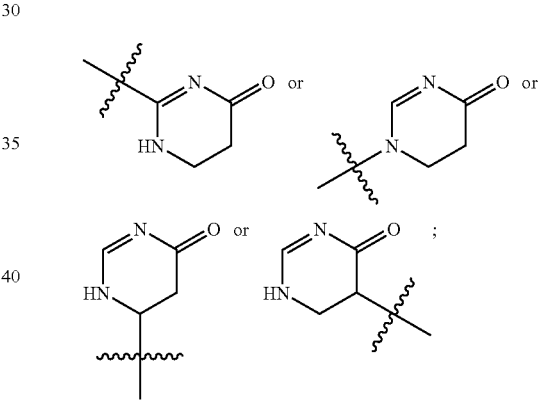
ix) a uracil ring having the formula:
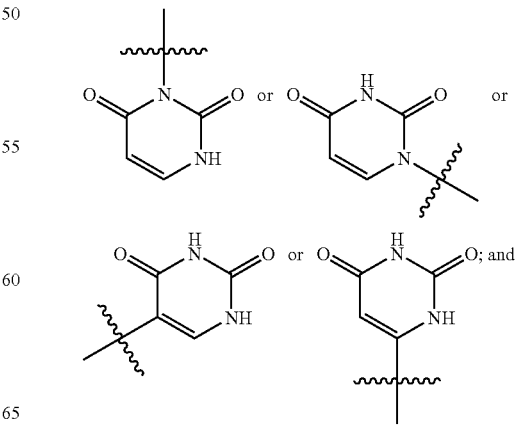

x) a triazinyl ring having the formula:

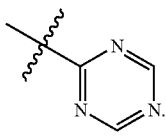

19. A polymer according to claim 16, wherein $R^4$ is a substituted or unsubstituted $C_5$ or $C_6$ heterocyclic or heteroaryl ring chosen from:

i) purinyl rings having the formula:

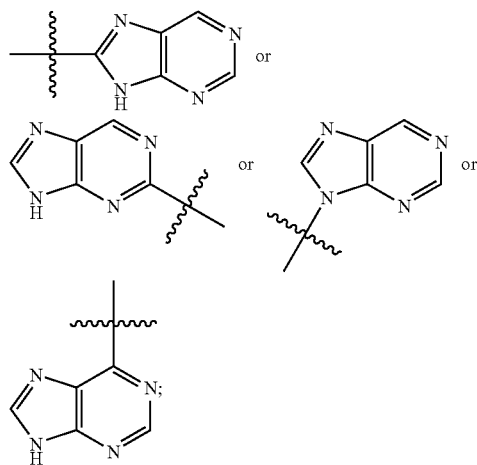

ii) amino purinyl rings having the formula:

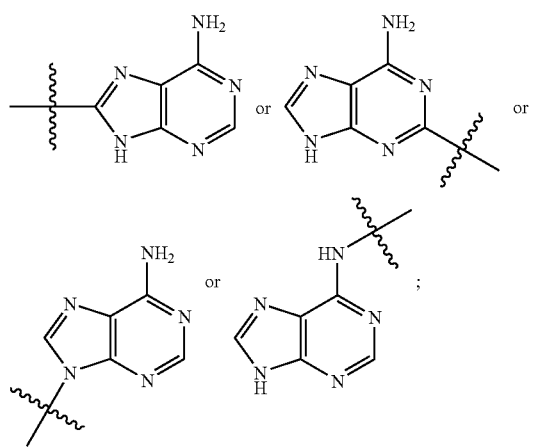

iii) aminopurinonyl rings having the formula:

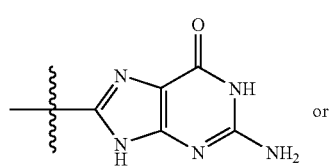

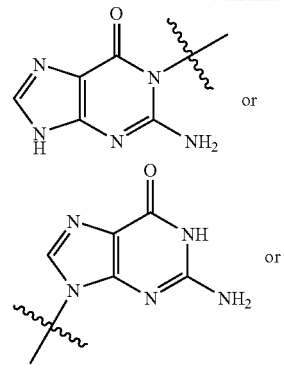

iv) pyrrolo[3,2-d]pyrimidinyl rings having the formula:

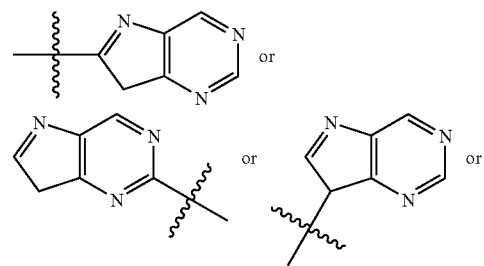

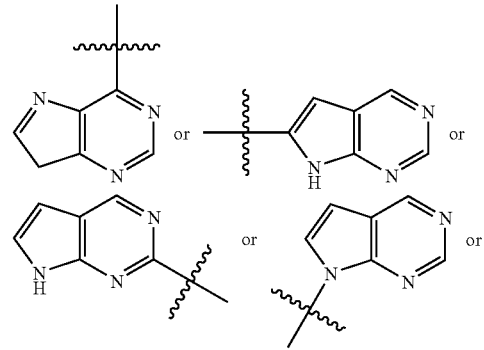

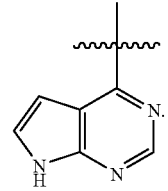

20. A polymer according to claim 1 wherein the $R^4$ unit is a $C_3$, $C_4$ or $C_5$ heterocyclic or heteroaryl ring substituted with one or more units chosen from:

i) $C_1$-$C_4$ linear or branched alkyl;
ii) —$NR^{6a}R^{6b}$;
iii) —$C(O)OR^7$;
iv) —$C(O)R^7$;
v) —$C(O)NR^{6a}R^{6b}$;
vi) —$NR^8C(O)NR^{6a}R^{6b}$;

vii) —NR⁸C(O)R⁷; and
viii) —NR⁸C(=NR⁸)NR⁶ᵃR⁶ᵇ;
R⁶ᵃ, R⁶ᵇ, R⁷, and R⁸ are each independently chosen from hydrogen, methyl or ethyl.

21. A polymer according to claim 1, wherein R⁴ has the formula:

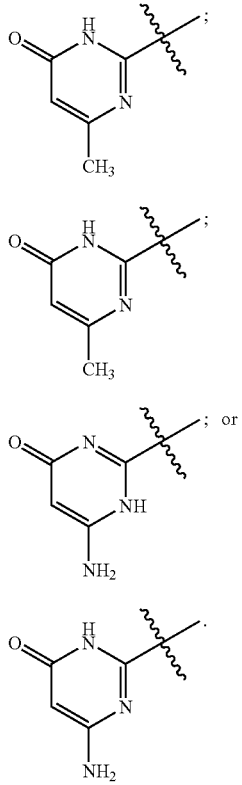

22. A polymer according to claim 1, wherein Y has the formula:

—(CR⁵ᵃR⁵ᵇ)ₛ— each R⁵ᵃ is independently chosen from hydrogen or methyl, R⁵ᵇ is hydrogen, the index s is from 2 to 6.

23. A polymer according to claim 22, wherein Y is a unit chosen from:
i) —CH₂CH₂—;
ii) —CH₂CH₂CH₂—;
iii) —CH(CH₃)CH₂—;
iv) —CH₂CH(CH₃)—;
v) —CH₂CH₂CH₂CH₂—;
vi) —CH₂CH₂CH₂CH₂CH₂—; and
vii) —CH₂CH₂CH₂CH₂CH₂CH₂—.

24. A polymer according to claim 23, wherein Y is —CH₂CH₂— (ethylene).

25. A polymer according to claim 1, wherein Y has the formula:

—[(CR⁵ᵃR⁵ᵇ)₂O]_w(CR⁵ᵃR⁵ᵇ)₂—

R⁵ᵃ and R⁵ᵇ are each independently hydrogen or methyl; the index w is from 1 to 4.

26. A polymer according to claim 25, wherein Y has the formula:

—[CH₂CH₂O]_wCH₂CH₂—.

27. A polymer according to claim 1, wherein Y has the formula:

[(CR⁵ᵃR⁵ᵇ)₂O]_w(CR⁵ᵃR⁵ᵇ)₂— wherein R⁵ᵃ is hydrogen or methyl provided at least one R⁵ᵃ unit is methyl; R⁵ᵇ is hydrogen; the index w is from 1 to 4.

28. A polymer according to claim 1, wherein linking unit L has the formula chosen from:

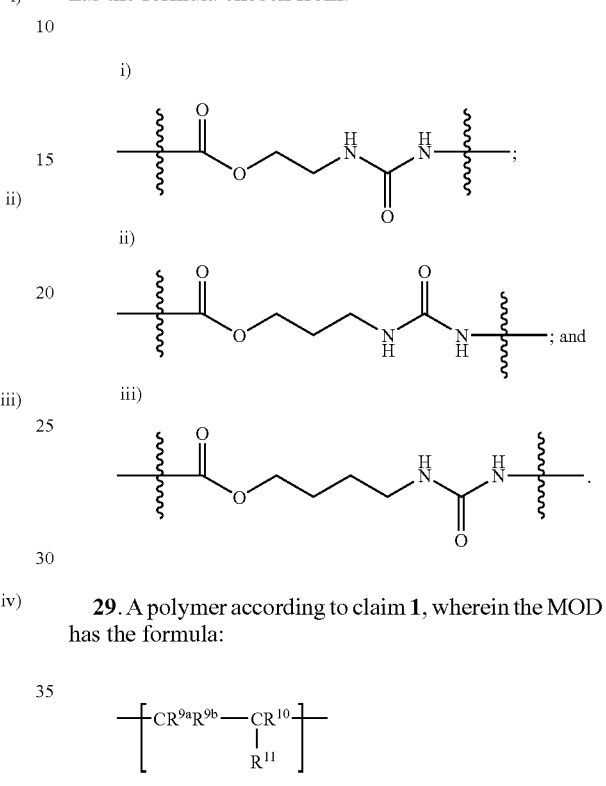

29. A polymer according to claim 1, wherein the MOD unit has the formula:

$$+[CR^{9a}R^{9b}-CR^{10}]+$$
$$\quad\quad\quad\quad\quad |$$
$$\quad\quad\quad\quad\quad R^{11}$$

wherein each R⁹ᵃ, R⁹ᵇ, and R¹⁰ are independently chosen from:
i) hydrogen; or
ii) C₁-C₄ alkyl;
R¹¹ is a unit chosen from:
i) hydrogen;
ii) C₁-C₄ linear or branched alkyl;
iii) —NR¹²ᵃR¹²ᵇ;
iv) —C(O)OR¹³;
v) —C(O)R¹³; and
vi) —C(O)NR¹²ᵃR¹²ᵇ;
wherein R¹²ᵃ, R¹²ᵇ, and R¹³ are each independently hydrogen or C₁-C₁₀ alkyl.

30. A polymer according to claim 29, wherein R⁹ᵃ and R⁹ᵇ are both hydrogen.

31. A polymer according to claim 29, wherein R¹⁰ is hydrogen or methyl.

32. A polymer according to claim 29, wherein R¹¹ has the formula —C(O)OR¹³.

33. A polymer according to claim 32, wherein R¹³ is chosen from methyl, ethyl, n-propyl, n-butyl, n-pentyl, and n-hexyl.

34. A polymer according to claim 1, wherein the XL unit has the formula:

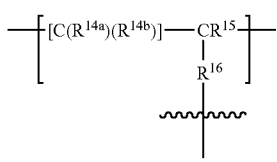

wherein the index n is from 1 to 4;

$R^{14a}$, $R^{14b}$, and $R^{15}$ are each independently chosen from:
i) hydrogen; and
ii) $C_1$-$C_4$ alkyl;

$R^{16}$ has the formula:

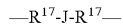

each $R^{17}$ is independently chosen from:
i) —$(CH_2)_pC(O)(CH_2)_q$—;
ii) —$(CH_2)_pC(O)O(CH_2)_q$—;
iii) —$(CH_2)_pOC(O)(CH_2)_q$—;
iv) —$(CH_2)_pNH(CH_2)_q$—;
v) —$(CH_2)_pC(O)NH(CH_2)_q$—;
vi) —$(CH_2)_pNHC(O)(CH_2)_q$—;
vii) —$(CH_2)_pNHC(O)NH(CH_2)_q$—;
viii) —$(CH_2)_pNHC(=NH)NH(CH_2)_q$—; and
ix) —$(CH_2)_p$—O—$(CH_2)_q$—;

the indices p and q have the value from 0 to 10; when p is 0 the —$(CH_2)$— units are absent; when q is 0 the —$(CH_2)$— units are absent;

J is a unit having the formula:

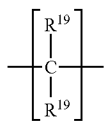

wherein each $R^{19}$ is each independently chosen from:
i) hydrogen;
ii) $C_1$-$C_{10}$ alkyl; or
iii) a unit capable of reacting with a HB monomer having the formula:

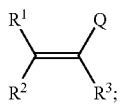

or MOD monomer having the formula:

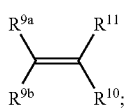

the $R^{19}$ unit having the formula:

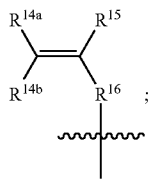

wherein $R^1$, $R^2$, $R^3$, $R^{9a}$, $R^{9b}$, $R^{10}$, $R^{14a}$, $R^{14b}$, $R^{15}$ and $R^{16}$ are the same as defined herein above.

35. A polymer according to claim 34, wherein the XL unit has the formula:

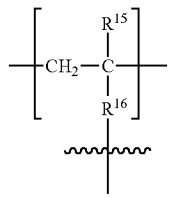

wherein each $R^{15}$ is independently hydrogen or methyl; $R^{16}$ has the formula:

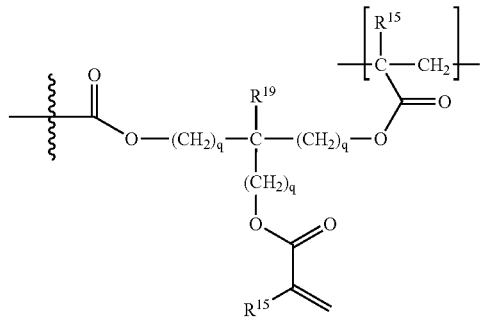

$R^{19}$ is hydrogen, methyl, or ethyl; each value for the index q is independently from 1 to 4.

36. A polymer according to claim 35, wherein each $R^{15}$ is methyl, $R^{19}$ is ethyl, and each index q is equal to 1.

37. A polymer according to claim 1, wherein the LX unit when linking two polymer chains has the formula:

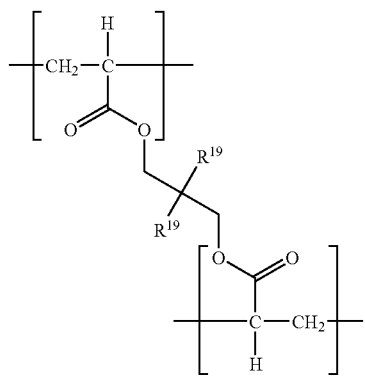

$R^{19}$ is hydrogen, methyl, ethyl, or a unit capable of forming a crosslink to another polymer chain.

38. A polymer according to claim 37, wherein the LX unit has the formula:

39. A polymer according to claim 1, having the formula:

$$-\!\!\left[C(R^1)(R^2)]-\overset{\overset{Q}{|}}{\underset{R^3}{C}}\right]_x\!\!\left[CR^{9a}R^{9b}\!-\!\underset{R^{11}}{CR^{10}}\right]_y\!\!\left[C(R^{14a})(R^{14b})]\!-\!\underset{R^{16}}{CR^{15}}\right]_z\!\!-$$

wherein the polymer comprises the following ratio:
x is from 0.5 to 5: y is from 90 to 99: z is from 0.5 to 5, such that the sum of x+y+z=100.

40. A polymer according to claim 39, wherein $R^1$, $R^2$, $R^3$, $R^{9a}$, $R^{9b}$, $R^{11}$, $R^{14a}$, $R^{14b}$, and $R^{15}$ are each independently hydrogen or methyl.

41. A polymer according to claim 40, wherein $R^1$, $R^2$, $R^{9a}$, $R^{9b}$, $R^{14}$, and $R^{14b}$ are hydrogen and $R^3$, $R^{11}$, and $R^{15}$ are methyl.

42. A polymer according to claim 39, wherein Q has the formula:

$$-[W]_h-[Y]_j-[Z]_k-R^4$$

W is chosen from —C(O)O— or —C(O)NH—;
Y is chosen from —(CH$_2$)$_s$— or —[(CH$_2$)$_t$O]$_w$(CH$_2$)$_s$—;
the index s is 2 or 3, the index t is 2 or 3; the index w is from 1 to 4;
Z is chosen from:
i) —C(O)—;
ii) —C(O)O—;
iii) —NH—;
iv) —C(O)NH—;
v) —NHC(O)—; or
vi) —NHC(O)NH—; and
$R^4$ is chosen from:

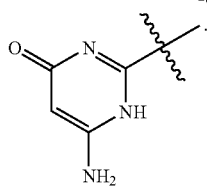

43. A polymer according to claim 39, wherein $R^{11}$ is chosen from:
a) —C(O)OH;
b) —C(O)OCH$_3$;
c) —C(O)OCH$_2$CH$_3$;
d) —C(O)OCH$_2$CH$_2$CH$_3$;
e) —C(O)OCH(CH$_3$)$_2$;
f) —C(O)OCH$_2$CH$_2$CH$_2$CH$_3$;
g) —C(O)OCH$_2$CH$_2$CH$_2$CH$_2$CH$_3$; and
h) —C(O)OCH$_2$CH$_2$CH$_2$CH$_2$CH$_2$CH$_3$.

44. A polymer according to claim 43, wherein $R^{11}$ is —C(O)OCH$_2$CH$_2$CH$_2$CH$_3$.

45. A polymer according to claim 39, wherein $R^{16}$ has the formula:

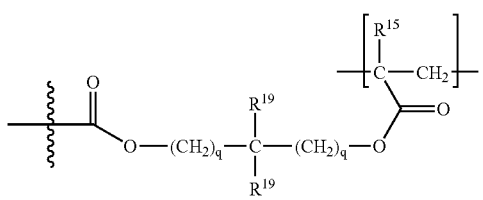

wherein $R^{15}$ is hydrogen or methyl,
each $R^{19}$ is each independently chosen from:
i) hydrogen;
ii) $C_1$-$C_{10}$ alkyl; or
iii) a unit capable of reacting with a HB monomer having the formula:

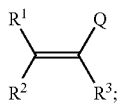

or MOD monomer having the formula:

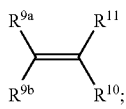

the $R^{19}$ unit having the formula:

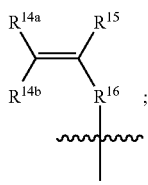

wherein $R^1$, $R^2$, $R^3$, $R^{9a}$, $R^{9b}$, $R^{10}$, $R^{14a}$, $R^{14b}$, $R^{15}$ and $R^{16}$ are the same as defined herein above.

46. A polymer according to claim 45, wherein $R^{16}$ has the formula:

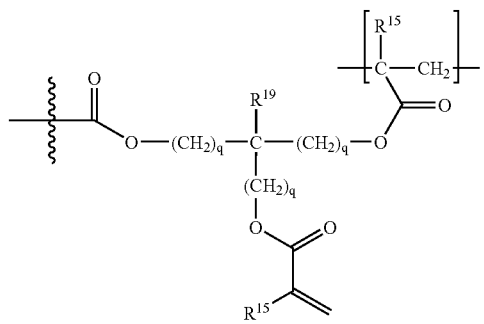

wherein $R^{19}$ is $C_1$-$C_4$ alkyl, and each of the indices q is equal to 1 or 2.

47. A polymer according to claim 39, having the formula:

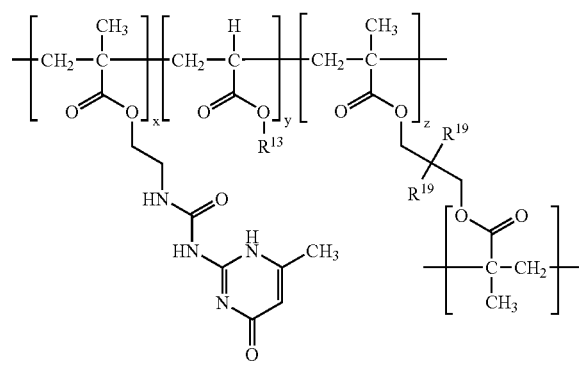

wherein $R^{13}$ is $C_1$-$C_6$ alkyl, $R^{19}$ is hydrogen, methyl, ethyl, or a unit capable of reacting with a HB monomer having the formula:

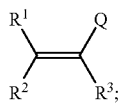

or MOD monomer having the formula:

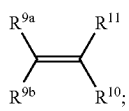

the $R^{19}$ unit capable of reacting has the formula:

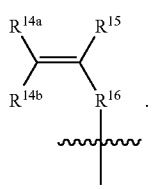

* * * * *

UNITED STATES PATENT AND TRADEMARK OFFICE
CERTIFICATE OF CORRECTION

PATENT NO. : 7,935,131 B2
APPLICATION NO. : 11/820693
DATED : May 3, 2011
INVENTOR(S) : Anthamatten et al.

Page 1 of 1

It is certified that error appears in the above-identified patent and that said Letters Patent is hereby corrected as shown below:

Col. 70 Line 46 Claim 37, line 1, "the LX unit" should read --the XL unit--; and Col. 71 Line 1 Claim 38, line 1, "the LX unit" should read --the XL unit--.

Signed and Sealed this
Fifth Day of July, 2011

David J. Kappos
*Director of the United States Patent and Trademark Office*